(12) United States Patent
Sakarya et al.

(10) Patent No.: US 12,237,053 B2
(45) Date of Patent: Feb. 25, 2025

(54) DETECTING CROSS-CONTAMINATION IN SEQUENCING DATA

(71) Applicant: GRAIL, Inc., Menlo Park, CA (US)

(72) Inventors: Onur Sakarya, Redwood City, CA (US); John Lamping, Los Altos, CA (US)

(73) Assignee: GRAIL, Inc., Menlo Park, CA (US)

(*) Notice: Subject to any disclaimer, the term of this patent is extended or adjusted under 35 U.S.C. 154(b) by 1345 days.

(21) Appl. No.: 16/019,315

(22) Filed: Jun. 26, 2018

(65) Prior Publication Data

US 2018/0373832 A1    Dec. 27, 2018

Related U.S. Application Data

(60) Provisional application No. 62/633,008, filed on Feb. 20, 2018, provisional application No. 62/534,868, filed on Jul. 20, 2017, provisional application No. 62/525,655, filed on Jun. 27, 2017.

(51) Int. Cl.
| | | |
|---|---|---|
| *G16B 5/20* | (2019.01) | |
| *C12Q 1/6806* | (2018.01) | |
| *G06N 20/00* | (2019.01) | |
| *G16B 5/00* | (2019.01) | |
| *G16B 20/20* | (2019.01) | |
| *G16B 30/00* | (2019.01) | |
| *G16B 30/10* | (2019.01) | |
| *G16B 30/20* | (2019.01) | |
| *G16B 40/10* | (2019.01) | |

(52) U.S. Cl.
CPC .............. *G16B 5/20* (2019.02); *C12Q 1/6806* (2013.01); *G16B 5/00* (2019.02); *G16B 20/20* (2019.02); *G16B 30/00* (2019.02); *G06N 20/00* (2019.01); *G16B 30/10* (2019.02); *G16B 30/20* (2019.02); *G16B 40/10* (2019.02)

(58) Field of Classification Search
CPC .......... G16B 5/00; G16B 30/00; G16B 30/10; G16B 40/10; G16B 30/20
See application file for complete search history.

(56) References Cited

U.S. PATENT DOCUMENTS

| | | |
|---|---|---|
| 2012/0264121 A1 | 10/2012 | Rava et al. |
| 2014/0127688 A1 | 5/2014 | Umbarger et al. |
| 2018/0237838 A1 | 8/2018 | Sakarya et al. |
| 2018/0373832 A1 | 12/2018 | Sakarya et al. |

FOREIGN PATENT DOCUMENTS

| | | | | |
|---|---|---|---|---|
| AU | 2015205935 A1 | * | 8/2015 | ............... C12Q 1/68 |
| WO | WO 2013/028699 A2 | | 2/2013 | |
| WO | WO 2014/074611 A1 | | 5/2014 | |
| WO | WO 2016/115307 A1 | | 7/2016 | |
| WO | WO 2018/150378 A1 | | 8/2018 | |

OTHER PUBLICATIONS

Flickinger et al., Detecting and Correcting Contamination in Genetic Data, 2016, University of Michigan, p. 1-90 (Year: 2016).*
Cibulskis et al., ContEst: estimating cross-contamination of human samples in next-generation sequencing data, 2011, 27(18), p. 2601-2602 and supplemental (Year: 2011).*
Stanford, Introduction to Statistical Inference—Bayesian Analysis, 2016, p. 20-1 to 20-4 (Year: 2016).*
Springer, Sequential probability ratio test, Encyclopedia of Mathematics, 2011, p. 1-3 (Year: 2011).*
Karoui et al., Getting more from digital SNP data, 2006, Statist. Med., 25, p. 3124-3133 (Year: 2006).*
Bergmann, E. et al., "Conpair: Concordance and Contamination Estimator for Matched Tumor-Normal Pairs" Bioinformatics 32(20), pp. 3196-3198.
Cibulskis, K. et al., "ContEst: Estimating Cross-Contamination of Human Samples in Next-Generation Sequencing Data," Bioinformatics, vol. 27, No. 18, Jul. 29, 2011, pp. 2601-2602.
Jun, G. et al., "Detecting and Estimating Contamination of Human DNA Samples in Sequencing and Array-Based Genotype Data," American Journal of Human Genetics, vol. 91, No. 5, Nov. 1, 2012, pp. 839-848.
Kim, S. et al., "Virmid: Accurate Detection of Somatic Mutations with Sample Impurity Inference," Genome Biology, vol. 14, No. 8, Aug. 29, 2013, 17 pages.
PCT International Search Report and Written Opinion, PCT Application No. PCT/US2018/039609, Sep. 28, 2018, 17 pages.
Theunert, C. et al., "Joint Estimation of Relatedness Coefficients and Allele Frequencies from Ancient Samples," Genetics, vol. 206, No. 2, Jun. 7, 2017, pp. 1025-1035.
U.S. Appl. No. 62/460,268, filed Feb. 17, 2017, Inventor Sakarya, O. et al., (copy not enclosed).

(Continued)

*Primary Examiner* — Kaitlyn L Minchella
(74) *Attorney, Agent, or Firm* — Fenwick & West LLP

(57) ABSTRACT

Detecting cross-contamination between test samples used for determining cancer in a subject is beneficial. To detect cross-contamination, test sequences including at least one single nucleotide polymorphism are prepared using genome sequencing techniques. Some of the test sequences can be filtered to improve accuracy and precision. A prior contamination probability for each test sequence is determined based on a minor allele frequency. A contamination model including a likelihood test is applied to a test sequence. The likelihood test obtains a current contamination probability representing the likelihood that the test sample is contaminated. The contamination model can also determine a likelihood that the sample includes loss of heterozygosity representing the likelihood that the test sequence is contaminated. Test samples that are contaminated are removed. A source for the contaminated test sample can be found by comparing contaminated test sequences to other test sequences.

19 Claims, 36 Drawing Sheets

(56) References Cited

OTHER PUBLICATIONS

PCT International Search Report and Written Opinion, PCT Application No. PCT/IB2018/050979, Apr. 18, 2018, 16 pages.

Sakarya, O. et al., "Conta: methods for detecting trace amounts of contamination," Abstract, ISMB conference, (Jul. 21-24, 2017), one page.

Sakarya, O. et al., "Conta: methods for detecting trace amounts of contamination," Poster, ISMB conference, (Jul. 21-24, 2017), one page.

United States Office Action, U.S. Appl. No. 15/900,645, Jan. 21, 2021, 30 pages.

Xu, C. et al., "Detecting very low allele fraction variants using targeting DNA sequencing and a novel molecular barcode-aware variant caller," BMC Genomics 18(5), Jan. 3, 2017, pp. 1-11.

PCT International Search Report and Written Opinion, PCT Application No. PCT/US2021/050995, Mar. 3, 2022, 21 pages.

PCT Invitation to Pay Additional Fees, PCT Application No. PCT/US2021/050995, Jan. 10, 2022, 15 pages.

Shiraishi, M. et al. "High-Speed Conversion of Cytosine to Uracil in Bisulfite Genomic Sequencing Analysis of DNA Methylation." DNA Research, vol. 11, No. 6, Dec. 1, 2004, pp. 409-415.

Ignatiadis, M. et al., "Circulating Tumor Cells and Circulating Tumor DNA: Challenges and Opportunities on the Path to Clinical Unity," Clinical Cancer Research 21(21), Nov. 1, 2015, pp. 4786-4800.

Surdhar, G.K, "Cycle Sequencing of PCR Products," PCT Mutation Detection Protocols, Methods in Molecular Biology, vol. 187, 2002, pp. 65-72.

United States Office Action, U.S. Appl. No. 15/900,645, Feb. 9, 2023, 24 pages.

United States Office Action, U.S. Appl. No. 15/900,645, Jul. 21, 2022, 30 pages.

* cited by examiner

Screenshot 2600

FIG. 26

DETECTING CROSS-CONTAMINATION IN SEQUENCING DATA

CROSS REFERENCE TO RELATED APPLICATIONS

This application claims the benefit of priority to U.S. Provisional Application No. 62/525,655, filed Jun. 27, 2017, U.S. Provisional Application No. 62/534,868, filed Jul. 20, 2017, and U.S. Provisional Application No. 62/633,008, filed Feb. 20, 2018, all of which are incorporated herein by reference in their entirety for all purposes.

BACKGROUND

1. Field of Art

This application relates generally to detecting contamination in a sample, and more specifically to detecting contamination in a sample including targeted sequencing used for early detection of cancer.

2. Description of the Related Art

Next generation sequencing-based assays of circulating tumor DNA must achieve high sensitivity and specificity in order to detect cancer early. Early cancer detection and liquid biopsy both require highly sensitive methods to detect low tumor burden as well as specific methods to reduce false positive calls. Contaminating DNA from adjacent samples can compromise specificity which can result in false positive calls. In various instances, compromised specificity can be because rare SNPs from the contaminant may look like low level mutations. Methods currently exist for detecting and estimating contamination in whole genome sequencing data, typically from relatively low-depth sequencing studies. However, existing methods are not designed for detection of contamination in sequencing data from cancer detection samples, which typically require high-depth sequencing studies and include tumor-derived mutations (e.g., single base mutations and/or copy number variations (CNVs)) that may be present at varying frequencies (e.g., clonal and/or sub-clonal tumor-derived mutations). There is a need for new methods of detecting cross-sample contamination in sequencing data from a test sample used for cancer detection.

SUMMARY

The systems and methods described herein can be used to determine cross-contamination between test samples used for determining cancer in a subject. The test samples are prepared using genome sequencing techniques. Each test sample includes a number of test sequences including at least one single nucleotide polymorphism that can be indicative of cancer. The system can filter the test sequences to remove at least some of the SNPs from the test sequences based on a variety of criteria. The remaining SNPs from the test sequences form a population of SNPs.

The system determines a prior contamination probability for each SNP remaining in the population based on a minor allele frequency for each of the SNPs that remain. To determine contamination, the system can apply a contamination model including a least one likelihood test to a test sequence of the test sample. The likelihood test obtains a current contamination probability representing the likelihood that the test sequence is contaminated. In another example, the contamination model determines a likelihood that the sample includes loss of heterozygosity representing the likelihood that the test sequence is contaminated. In response, the system can remove the test sequence from the population if the test sequence is determined to be contaminated. Additionally, the system can determine a source of the contaminated test sequence. To determine the source of the contaminated test sequence, the system compares the contaminated test sequences to test sequences from other samples.

BRIEF DESCRIPTION OF DRAWINGS

Figure (FIG. 1 is a flowchart of a method for preparing a nucleic acid sample for sequencing, according to one example embodiment.

FIG. 26 is a screenshot of a portion of the output file of FIG. 14 that shows the analysis data for two contamination events in the baseline/normal sample dataset, according to one example embodiment.

Figure 1:
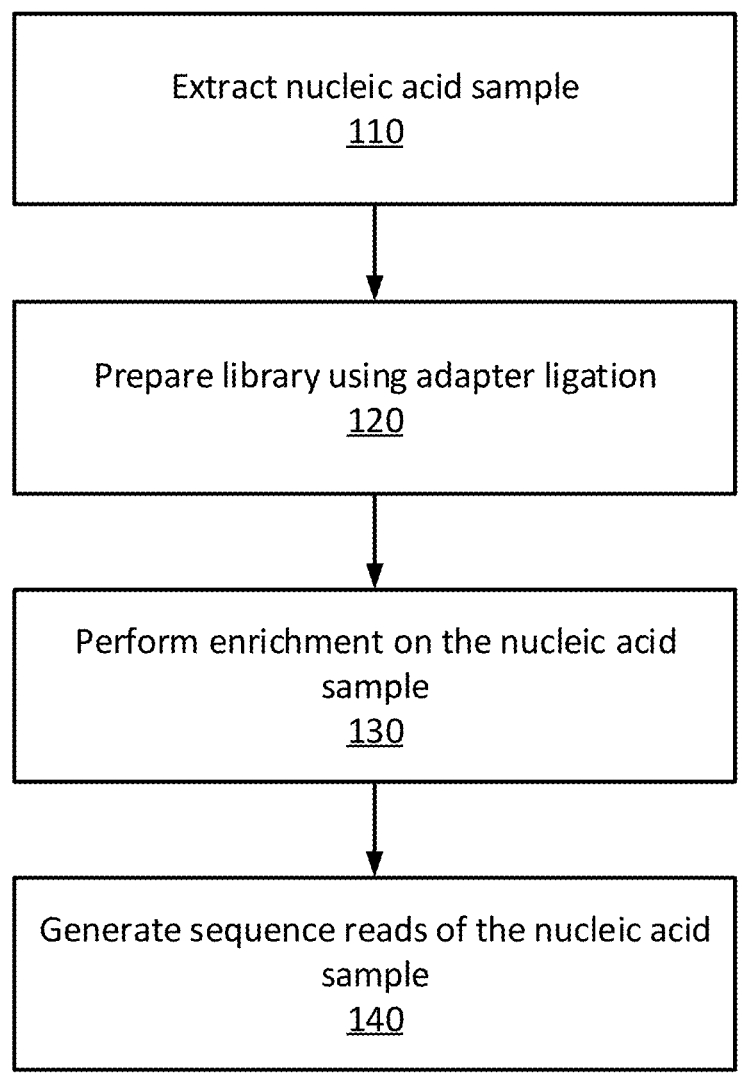

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. Definitions

The term "individual" refers to a human individual. The term "healthy individual" refers to an individual presumed to not have cancer or disease. The term "subject" refers to an individual who is known to have, or potentially has, cancer or disease.

The term "sequence reads" refers to nucleotide sequences read from a sample obtained from an individual. Sequence reads can be obtained through various methods known in the art.

The term "read segment" or "read" refers to any nucleotide sequences including sequence reads obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

The term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

The term "single nucleotide polymorphism" or "SNP" refers to a position on the genome where significant fraction of the population has a substitution of one nucleotide to a different nucleotide at a position (e.g., site) of a nucleotide sequence, e.g., a sequence read from an individual. For example, at a specific base site, the nucleobase C may appear in most individuals, but in a minority of individuals, the position is occupied by base A. There is a SNP at this specific site.

The term "indel" refers to any insertion or deletion of one or more base pairs having a length and a position (which may also be referred to as an anchor position) in a sequence read. An insertion corresponds to a positive length, while a deletion corresponds to a negative length.

The term "mutation" refers to one or more SNVs or indels.

The term "true positive" refers to a mutation that indicates real biology, for example, the presence of potential cancer, disease, or germline mutation in an individual. True positives are not caused by mutations naturally occurring in healthy individuals (e.g., recurrent mutations) or other sources of artifacts such as process errors during assay preparation of nucleic acid samples.

The term "false positive" refers to a mutation incorrectly determined to be a true positive. Generally, false positives may be more likely to occur when processing sequence reads associated with greater mean noise rates or greater uncertainty in noise rates.

The term "cell-free nucleic acid," "cell-free DNA," or "cfDNA" refers to nucleic acid fragments that circulate in an individual's body (e.g., bloodstream) and originate from one or more healthy cells and/or from one or more cancer cells.

The term "circulating tumor DNA" or "ctDNA" refers to nucleic acid fragments that originate from tumor cells or other types of cancer cells, which may be released into an individual's bloodstream as result of biological processes such as apoptosis or necrosis of dying cells or actively released by viable tumor cells.

The term "genomic nucleic acid," "genomic DNA," or "gDNA" refers to nucleic acid including chromosomal DNA that originates from one or more healthy cells.

The term "alternative allele" or "ALT" refers to an allele having one or more mutations relative to a reference allele, e.g., corresponding to a known gene.

The term "minor allele" or "MIN" refers to the second most common allele in a given population.

The term "sequencing depth" or "depth" refers to a total number of read segments from a sample obtained from an individual at a particular position of the genome.

The term "allele depth" or "AD" or "DP" refers to a number of read segments in a sample that supports an allele in a population. The terms "AAD", "MAD" refer to the "alternate allele depth" (i.e., the number of read segments that support an ALT) and "minor allele depth" (i.e., the number of read segments that support a MIN), respectively.

The term "contaminated" refers to a test sample that is contaminated with at least some portion of a second test sample. That is, a contaminated test sample unintentionally includes DNA sequences from an individual that did not generate the test sample. Similarly, the term "uncontaminated" refers to a test sample that does not include at least some portion of a second test sample.

The term "contamination level" refers to the degree of contamination in a test sample. That is, the contamination level the number of reads in a first test sample from a second test sample. For example, if a first test sample of 1000 reads includes 30 reads from a second test sample, the contamination level is 3.0%.

The term "contamination event" refers to a test sample being called contaminated. Generally, a test sample is called contaminated if the determined contamination level is above a threshold contamination level and the determined contamination level is statistically significant.

The term "allele frequency" or "AF" refers to the frequency of a given allele in a sample. The terms "AAF", "MAF" refer to the "alternate allele frequency" and "minor allele frequency", respectively. The AF may be determined by dividing the corresponding AD of a sample by the depth of the sample for the given allele.

II. Example Assay Protocol

FIG. 1 is a flowchart of a method 100 for preparing a nucleic acid sample for sequencing according to one embodiment. The method 100 includes, but is not limited to, the following steps. For example, any step of the method 100 may comprise a quantitation sub-step for quality control or other laboratory assay procedures known to one skilled in the art.

In step 110, a nucleic acid sample (DNA or RNA) is extracted from a subject. In the present disclosure, DNA and RNA may be used interchangeably unless otherwise indicated. That is, the following embodiments for using error source information in variant calling and quality control may be applicable to both DNA and RNA types of nucleic acid sequences. However, the examples described herein may focus on DNA for purposes of clarity and explanation. The sample may be any subset of the human genome, including the whole genome. The sample may be extracted from a subject known to have or suspected of having cancer. The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may require surgery. The extracted sample may comprise cfDNA and/or ctDNA. For healthy individuals, the human body may naturally clear out cfDNA and other cellular debris. If a subject has cancer or disease, ctDNA in an extracted sample may be present at a detectable level for diagnosis.

In step 120, a sequencing library is prepared. During library preparation, unique molecular identifiers (UMI) are added to the nucleic acid molecules (e.g., DNA molecules) through adapter ligation. The UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. During PCR amplification following adapter ligation, the UMIs are replicated along with the attached DNA fragment, which provides a way to identify sequence reads that came from the same original fragment in downstream analysis.

In step 130, targeted DNA sequences are enriched from the library. During enrichment, hybridization probes (also referred to herein as "probes") are used to target, and pull down, nucleic acid fragments informative for the presence or absence of cancer (or disease), cancer status, or a cancer classification (e.g., cancer type or tissue of origin). For a given workflow, the probes may be designed to anneal (or hybridize) to a target (complementary) strand of DNA or RNA. The target strand may be the "positive" strand (e.g., the strand transcribed into mRNA, and subsequently translated into a protein) or the complementary "negative" strand. The probes may range in length from 10 s, 100 s, or 1000 s of base pairs. In one embodiment, the probes are designed based on a gene panel to analyze particular mutations or target regions of the genome (e.g., of the human or another organism) that are suspected to correspond to certain cancers or other types of diseases. Moreover, the probes may cover overlapping portions of a target region. By using a targeted gene panel rather than sequencing all expressed genes of a genome, also known as "whole exome sequencing," the method 100 may be used to increase sequencing depth of the target regions, where depth refers to the count of the number of times a given target sequence within the sample has been sequenced. Increasing sequencing depth reduces required input amounts of the nucleic acid sample. After a hybridization step, the hybridized nucleic acid fragments are captured and may also be amplified using PCR.

In step 140, sequence reads are generated from the enriched DNA sequences. Sequencing data may be acquired from the enriched DNA sequences by known means in the art. For example, the method 100 may include next-generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLID sequencing), nanopore sequencing (Oxford Nanopore Technologies), or paired-end sequencing. In some embodiments, massively parallel sequencing is performed using sequencing-by-synthesis with reversible dye terminators.

In some embodiments, the sequence reads may be aligned to a reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene.

In various embodiments, a sequence read is comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome represent the likely location within the reference genome to which the nucleic acid fragment corresponds. An output file having SAM (sequence alignment map) format or BAM (binary) format may be generated and output for further analysis such as variant calling, as described below with respect to FIG. 2.

III. Example Processing System

Figure 2:
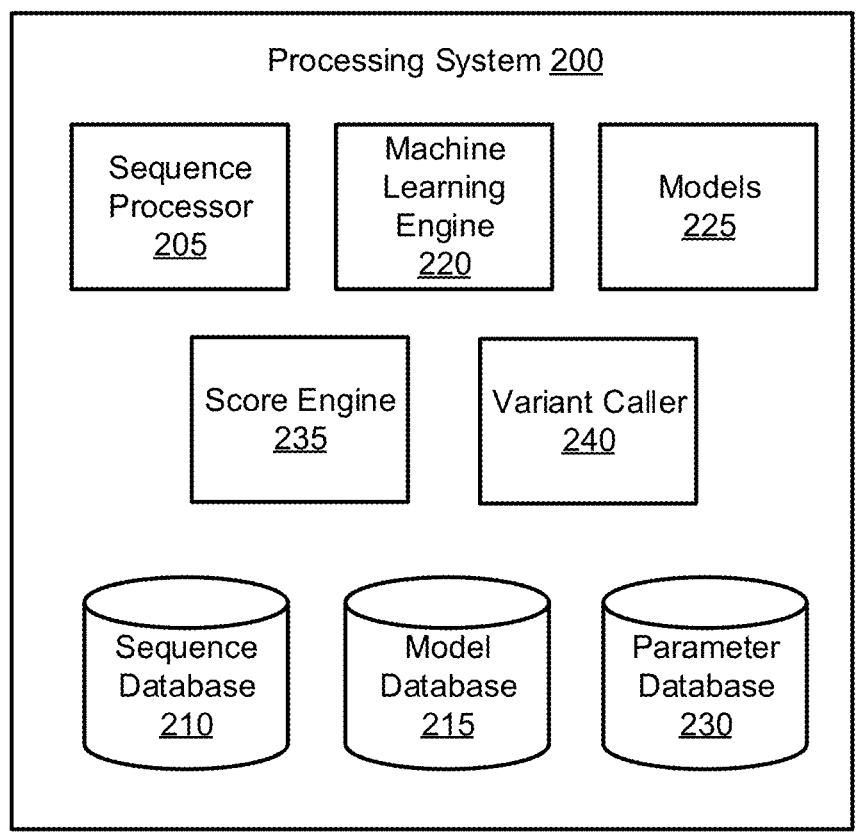
FIG. 2 is a block diagram of a processing system for processing sequence reads, according to one example embodiment.
Figure 3:
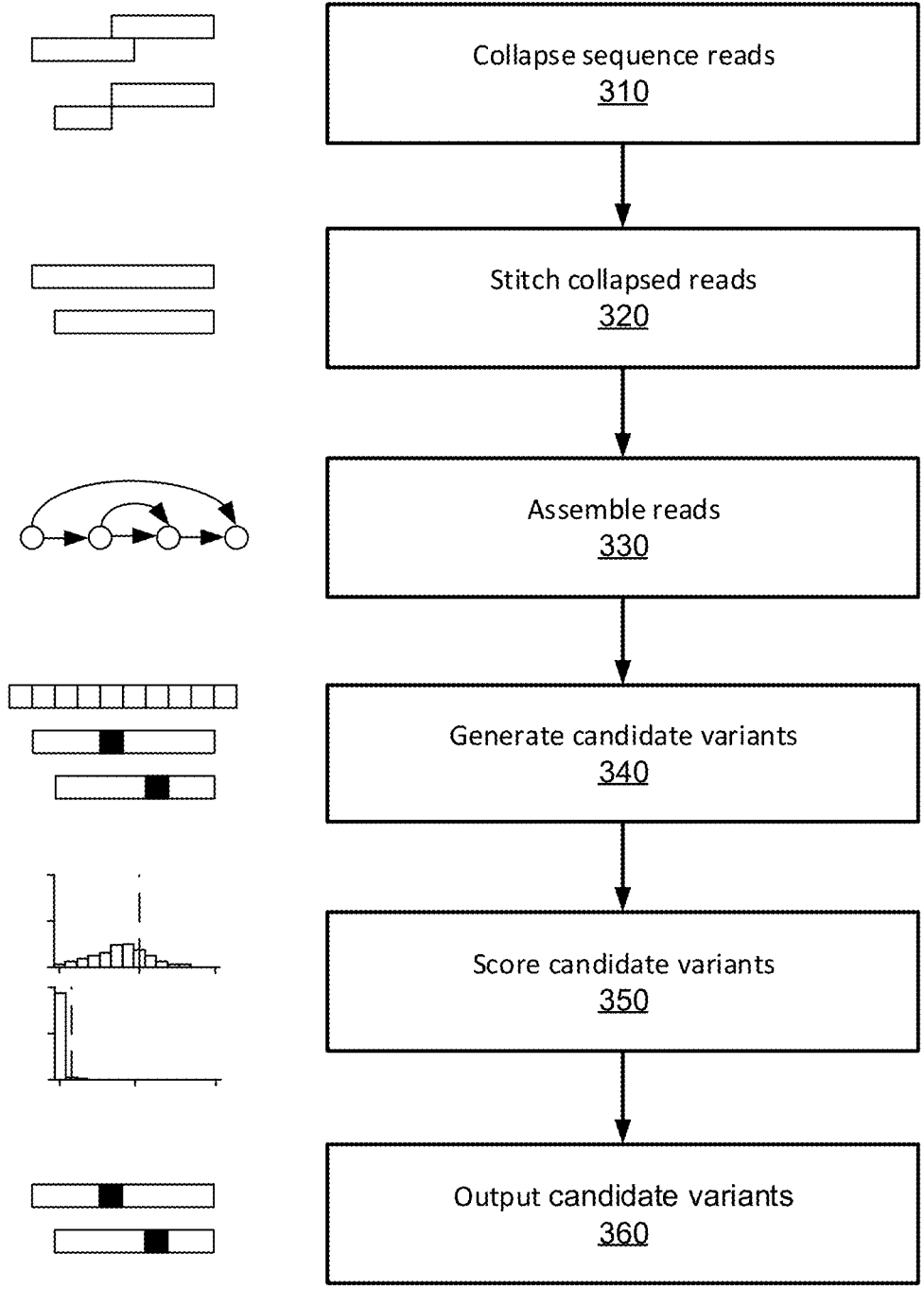
FIG. 3 is a flowchart of a method for determining variants of sequence reads, according to one example embodiment.

FIG. 2 is a block diagram of a processing system 200 for processing sequence reads according to one embodiment. The processing system 200 includes a sequence processor 205, sequence database 210, model database 215, machine learning engine 220, models 225, parameter database 230, score engine 235, and variant caller 240. FIG. 3 is a flowchart of a method 300 for determining variants of sequence reads according to one embodiment. In some embodiments, the processing system 200 performs the method 300 to perform variant calling (e.g., for SNPs) based on input sequencing data. Further, the processing system 200 may obtain the input sequencing data from an output file associated with a nucleic acid sample prepared using the method 100 described above. The method 300 includes, but is not limited to, the following steps, which are described with respect to the components of the processing system 200. In other embodiments, one or more steps of the method 300 may be replaced by a step of a different process for generating variant calls, e.g., using Variant Call Format (VCF), such as HaplotypeCaller, VarScan, Strelka, or SomaticSniper.

The processing system 200 can be any type of computing device that is capable of running program instructions. Examples of processing system 200 may include, but are not limited to, a desktop computer, a laptop computer, a tablet device, a personal digital assistant (PDA), a mobile phone or smartphone, and the like. In one example, when processing system is a desktop or laptop computer, models 225 may be executed by a desktop application. Applications can, in other examples, be a mobile application or web-based application configured to execute the models 225.

At step 310, the sequence processor 205 collapses aligned sequence reads of the input sequencing data. In one embodiment, collapsing sequence reads includes using UMIs, and optionally alignment position information from sequencing data of an output file (e.g., from the method 100 shown in FIG. 1) to collapse multiple sequence reads into a consensus sequence for determining the most likely sequence of a nucleic acid fragment or a portion thereof. Since the UMIs are replicated with the ligated nucleic acid fragments through enrichment and PCR, the sequence processor 205 may determine that certain sequence reads originated from the same molecule in a nucleic acid sample. In some embodiments, sequence reads that have the same or similar alignment position information (e.g., beginning and end positions within a threshold offset) and include a common UMI are collapsed, and the sequence processor 205 generates a collapsed read (also referred to herein as a consensus read) to represent the nucleic acid fragment. The sequence processor 205 designates a consensus read as "duplex" if the corresponding pair of collapsed reads have a common UMI, which indicates that both positive and negative strands of the originating nucleic acid molecule are captured; otherwise, the collapsed read is designated "non-duplex." In some embodiments, the sequence processor 205 may perform other types of error correction on sequence reads as an alternative to, or in addition to, collapsing sequence reads.

At step 320, the sequence processor 205 stitches the collapsed reads based on the corresponding alignment position information. In some embodiments, the sequence processor 205 compares alignment position information between a first read and a second read to determine whether nucleotide base pairs of the first and second reads overlap in the reference genome. In one use case, responsive to determining that an overlap (e.g., of a given number of nucleotide bases) between the first and second reads is greater than a threshold length (e.g., threshold number of nucleotide bases), the sequence processor 205 designates the first and second reads as "stitched"; otherwise, the collapsed reads are designated "unstitched." In some embodiments, a first and second read are stitched if the overlap is greater than the threshold length and if the overlap is not a sliding overlap. For example, a sliding overlap may include a homopolymer run (e.g., a single repeating nucleotide base), a dinucleotide run (e.g., two-nucleotide base sequence), or a trinucleotide run (e.g., three-nucleotide base sequence), where the homopolymer run, dinucleotide run, or trinucleotide run has at least a threshold length of base pairs.

At step 330, the sequence processor 205 assembles reads into paths. In some embodiments, the sequence processor 205 assembles reads to generate a directed graph, for example, a de Bruijn graph, for a target region (e.g., a gene). Unidirectional edges of the directed graph represent sequences of k nucleotide bases (also referred to herein as "k-mers") in the target region, and the edges are connected by vertices (or nodes). The sequence processor 205 aligns collapsed reads to a directed graph such that any of the collapsed reads may be represented in order by a subset of the edges and corresponding vertices.

At step 340, the variant caller 240 generates candidate variants from the paths assembled by the sequence processor 205. In one embodiment, the variant caller 240 generates the candidate variants by comparing a directed graph (which may have been compressed by pruning edges or nodes in step 310) to a reference sequence of a target region of a genome. The variant caller 240 may align edges of the directed graph to the reference sequence, and records the genomic positions of mismatched edges and mismatched nucleotide bases adjacent to the edges as the locations of candidate variants. Additionally, the variant caller 240 may generate candidate variants based on the sequencing depth of a target region. In particular, the variant caller 240 may be more confident in identifying variants in target regions that have greater sequencing depth, for example, because a greater number of sequence reads help to resolve (e.g., using redundancies) mismatches or other base pair variations between sequences. In some embodiments, the variants can be SNPs.

Further, multiple different models may be stored in the model database 215 or retrieved for application post-training. For example, a model is trained to model SNP noise rates, a model is trained to filter SNPs, a model is trained to verify contamination detection, a model is trained to detect loss of heterozygosity, etc. Further, the score engine 235 may use parameters of the model 225 to determine a likelihood of one or more true positives or contamination in a sequence read. The score engine 235 may determine a quality score (e.g., on a logarithmic scale) based on the likelihood. For example, the quality score is a Phred quality score $Q=-10 \cdot \log_{10} P$, where P is the likelihood of an incorrect candidate variant call (e.g., a false positive).

At step 350, the score engine 235 scores the candidate variants based on the model 225 or corresponding likelihoods of true positives, contamination, quality scores, etc. Training and application of the model 225 are described in more detail below.

At step 360, the processing system 200 outputs the candidate variants. In some embodiments, the processing system 200 outputs some or all of the determined candidate variants along with the corresponding scores. Downstream systems, e.g., external to the processing system 200 or other components of the processing system 200, may use the candidate variants and scores for various applications including, but not limited to, predicting the presence of cancer, predicting contamination in test sequences, predicting noise levels, or germline mutations.

IV. Example Contamination Detection Workflow

Figure 4:
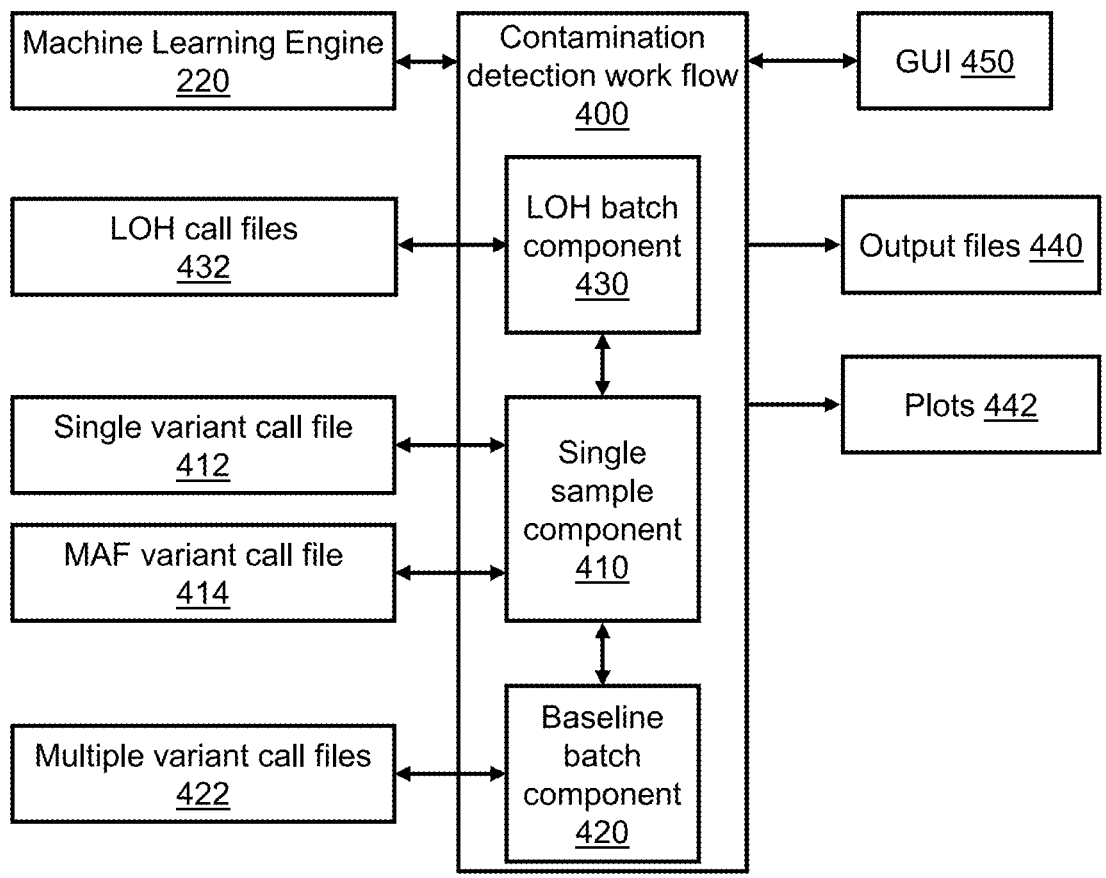
FIG. 4 illustrates a block diagram of a contamination detection application and workflow for detecting and calling contamination in a test sample, according to one example embodiment.

FIG. 4 is a diagram of a contamination detection workflow 400 executing on the processing system 200 for detecting and calling contamination, in accordance with one embodiment.

In the illustrated example, contamination detection workflow 400 includes a single sample component 410, a baseline batch component 420, and a loss of heterozygosity (LOH) batch component 430. Single sample component 410 of contamination detection workflow 400 is informed, for example, by the contents of a single variant call file 442 and a minor allele frequencies (MAF) variant call file 444 called by the variant caller 240. The single variant call file 412 is the variant call file for a single target sample. The MAF variant call file 414 is the MAF variant call file for any number of SNP population allele frequencies AF.

Baseline batch component 420 of contamination detection workflow 400 generates a background noise baseline for each SNP from uncontaminated samples as another input to single sample component 410. Generating a background noise baseline using a contamination noise baseline workflow is described in more detail in regards to FIG. 19. Baseline batch component 420 is informed, for example, by the contents of multiple variant call files 422 called by the variant caller 240. The multiple variant call files 422 can be the variant call files of multiple samples.

LOH batch component 430 of contamination detection workflow 400 determines a LOH in samples as another input to the single sample component 410. LOH batch component 430 is informed, for example, by the contents of LOH call files 432. The LOH call files are call files for a plurality of alleles previously determined to include SNPs with LOH in the sample. The LOH call files can be called by the variant caller 240 and stored in the sequence database 210.

In one embodiment, the contamination detection workflow 400 can generate output files 440 and/or plots from sequencing data processed by contamination detection algorithm. For example, contamination detection workflow 400 may generate log-likelihood data and/or display log-likelihood plots 442 as a means for evaluating a DNA test sample for contamination. Data processed by contamination detection workflow 400 can be visually presented to the user via a graphical user interface (GUI) 450 of the processing system 200. For example, the contents of output files 440 (e.g., a text file of data opened in Excel) and log-likelihood plots 442 can be displayed in GUI 450.

In another embodiment, the contamination detection workflow 400 may use the machine learning engine 220 to improve contamination detection. Various training datasets (e.g., parameters from parameter database 230, sequences from sequence database 210, etc.) may be used to supply information to the machine learning engine 220 as described herein. In accordance with this embodiment, the machine learning engine 220 may be used to train a contamination noise baseline to identify a noise threshold, detect loss of heterozygosity, and determine the limit of detection (LOD) for contamination detection.

Single sample component 410 of contamination detection workflow 400 is, for example, a runnable script that is used to estimate contamination in a sample. By contrast, baseline batch component 430 of contamination detection workflow 400 is, for example, a runnable script that is used for generating estimates across a batch of samples, and may also be used to generate the noise model across these samples (if the input batch is healthy). Similarly, LOH batch component 430 of contamination detection model is, for example, a runnable script that is used for generating estimates across a batch of samples, and may be used to determine the LOH in single samples based on the generated estimates.

V. Detecting Contamination of a Sample

In one embodiment, the contamination detection workflow 400 may be based on a model for estimating contamination. In one embodiment, the model is a maximum likelihood model (herein referred to as the likelihood model) for detecting contamination in sequencing data from a test sample. However, in other examples, the model can be any other estimation model such as an M-estimator, maximum spacing estimation, method of support, etc.

In one example, the likelihood model determines contamination by calculating the probability of observing a MAF of a sample at a given contamination level α and, subsequently, determining if the sample is contaminated. In some embodiments, the likelihood model is informed by prior probabilities of contamination that are first calculated for each SNP in the sample based on the genotype of previously observed contaminated samples.

Further, the contamination detection workflow 400 can, in some cases, determine the likely source of contamination for the observed sample. That is, the likelihood model can compare sequencing data from several contaminated samples to determine a source of contamination. The likelihood model can be informed by prior probabilities of contamination from other samples with a known genotype to identify a likely source of contamination.

In one example, the contamination detection workflow 400 is used in a sequencing-based variant calling workflow for early detection of cancer. For example, in a sequencing-based variant calling assay, analysis of sequence data for contamination is performed prior to variant calling. If a contamination call is made (i.e., a contamination event is detected), the contaminated sample can be discarded and a second aliquot of the original sample can then be processed for sequencing and variant calling.

V.A Probability of Contamination for a Single SNP

The contamination detection workflow 400 determines a probability that a sample is contaminated using prior probabilities and observed sequencing data. In some examples, the observed sequencing data can be included in a test sample call file (such as single variant call file 412), a LOH call file (such as LOH call file 432) and a population call file (such as MAF call file 414). The prior probabilities of contamination can be determined based on the observed sequencing data. Here, for purpose of example, the probability of contamination for a single SNP is based on a samples minor allele frequency MAF and the error rate of previously observed homozygous SNPs. In some embodiments, the contamination detection workflow 400 can additionally or alternatively use alternate allele frequency, noise rates, read depths, etc. to determine a contamination probability.

Contamination detection workflow 400 compares the probability of observing data in the test sequences using two different models. In one model, there is no contamination and any reads with alternative alleles at the site are either the result of noise in the test sequences or of heterozygosity of the test sequences at a site. In the other model, there is contamination of the test sample and test sequences with alternative alleles can be the result of correctly reading a contaminating DNA strand. In this context, contamination detection workflow 400 calculates a ratio between the likelihood the test sample is contaminated and the likelihood the test sample is uncontaminated using the two models. Based on the ratio, contamination detection workflow can determine if the test sample is contaminated or uncontaminated.

In one embodiment, the probability of contamination at a single SNP site for a given set of data D is calculated as:

$$P(\alpha|D) = P(\alpha) \cdot P(D|\alpha) \tag{1}$$

where $P(\alpha|D)$ is the probability of observing the contamination level $\alpha$ given the data D, $P(D|\alpha)$ is the probability of observing the data given the contamination level $\alpha$, and $P(\alpha)$ is the probability of the contamination level $\alpha$. Therefore, in an example where there is no contamination in the test sample, the probability of contamination in a test sample can be represented as:

$$P(\alpha=0|D) = P(D|\alpha=0) \cdot P(\alpha=0) \tag{2}$$

where $\alpha=0$ indicates that the contamination level $\alpha$ is 0.0%

In one example, the data D for an SNP in a test sample is represented below in Table 1.

TABLE 1

Data for an SNP in a test sample.

| | |
|---|---|
| SNP Identifier | RS2237290 |
| Chromosome Position | 7: 13952609 |
| Global MAF | 0.3896 |
| ε for A→T | $3 \cdot 10^{-5}$ |
| ε for T→A | $9 \cdot 10^{-5}$ |
| Test Sample Depth | 50 |
| Minor Allele Depth | 5 | where ε is the probability of a specific error or mutation at the SNP site. In other examples the data D can include any number of additional or fewer elements such that contamination detection workflow 400 can determine contamination in a test sample.

In one embodiment, in test samples where the contamination level is non-zero, the probability of observing data D with a contamination level $\alpha$ for a given set of data D ($P(D|\alpha)$) is further based on the genotype of the contaminant $G_C$ and the genotype of the host $G_H$ (the source of the test sample). That is, the probability of observing data D given a contamination level $\alpha$ can be represented as:

$$P(D|\alpha) = \Sigma_{G_H,G_C} P(G_H) \cdot P(G_C) \cdot P(D|\alpha p) \tag{3}$$

where $P(G_C)$ is the probability that the contamination at the SNP site will be the type associated with the genotype of the contaminant at that site, $P(G_H)$ is the probability that the contamination at the site will be the genotype of the host at that site, and $P(D|\alpha)$ is the probability of observing the data D at a contamination level $\alpha$. Here, the set of characteristics p include the probability of an SNP mutation ε for the SNP site and the contamination level $\alpha$ but can include any other characteristics of the test sample. The summation over the genotypes indicates that the probability of observing data at a contamination level $\alpha$ includes contributions based on the three possible genotypes of the contaminant and host (A/A, A/B, and B/B).

For a given site the probability of observing the data at a given contamination level can alpha can be represented with a generic site specific model. The generic site specific model can be represented as:

$$P(D|\alpha) = P(AA_{host}) \cdot P(AA_{cont}) \cdot P(D|p=\varepsilon) + \tag{4}$$
$$\ldots P(AA_{host}) \cdot P(AB_{cont}) \cdot P\left(D \mid p=\varepsilon+\frac{\alpha}{2}\right) +$$
$$\ldots P(AA_{host}) \cdot P(BB_{cont}) \cdot P(D \mid p=\varepsilon+\alpha) +$$
$$\ldots P(BB_{host}) \cdot P(BB_{cont}) \cdot P(D \mid p=\varepsilon)$$

where AA is a homozygous reference allele, AB is a heterozygous allele, BB is a homozygous alternative allele, the subscript "host" represents the genotype of the host $G_H$, the subscript "cont" represents the genotype of the contaminant, ε is the probability of observing a specific mutation, and a is the contamination level.

In some cases, the generic site specific model can be modeled with a binomial distribution. For example, for a specific case from the generic site specific model, the probability of observing the data D at a given contamination level alpha can be represented as:

$$P(D|\alpha) = P(D|AA_{host}, AB_{cont}, \alpha) = \text{binomial}(DP, MAD, \alpha/2+\varepsilon) \tag{5}$$

where "binomial" is the binomial probability of observing the data based on depth DP and minor allele depth MAD (minor allele depth) of the test sample, the genotype of the host (A/A), the genotype of the contaminant (A/B), the contamination level $\alpha$, and the probability of observing a specific error or mutation ε.

Figure 5A:
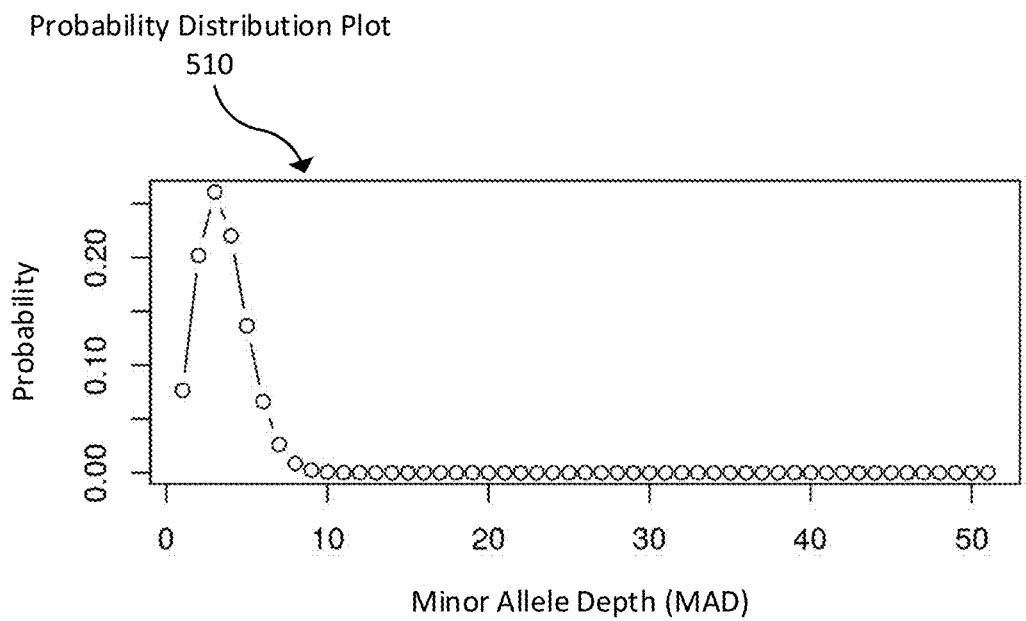
FIG. 5A-5F are probability distribution plots showing the probability of observing data at a given contamination level as a function of minor allele depth for different contamination levels and probabilities of observing specific mutation.

For example, FIG. 5A is probability distribution plot 510 for a test sample with a contamination level $\alpha$ of 10% and a probability of observing a specific mutation ε of 0.01%. In this plot, the minor allele depth is on the x-axis and the probability based on the binomial distribution (similar to Eqn. 4) is on the y-axis. Therefore, the plot shows the probability of observing a minor allele depth MAD given the contamination level alpha, the SNP mutation probability epsilon, a genotype of the host of A/A and a genotype of the contaminant of A/B.

Figure 5B:
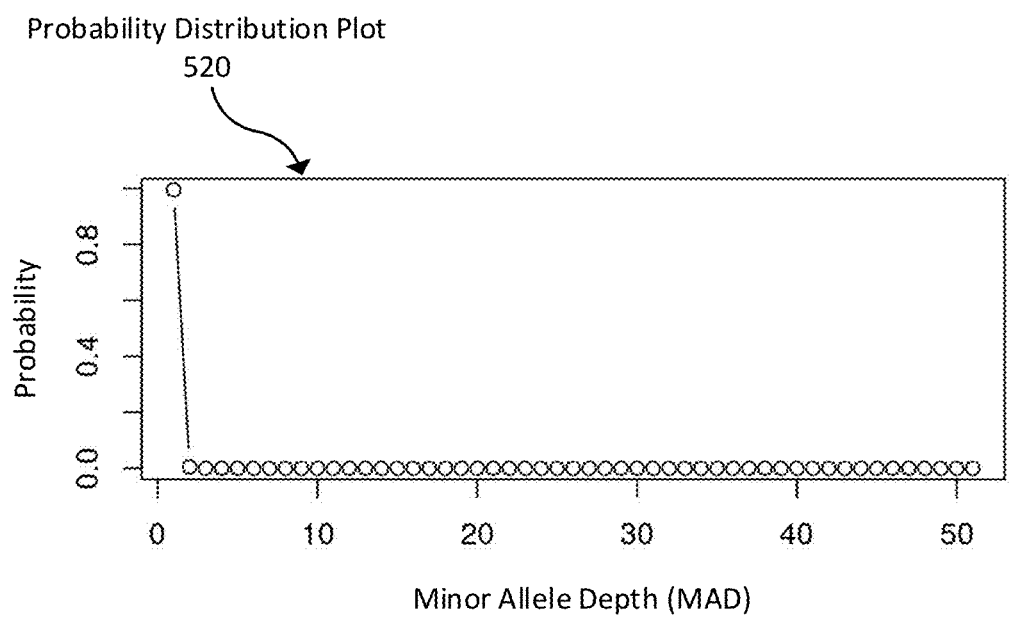
Figure 5C:
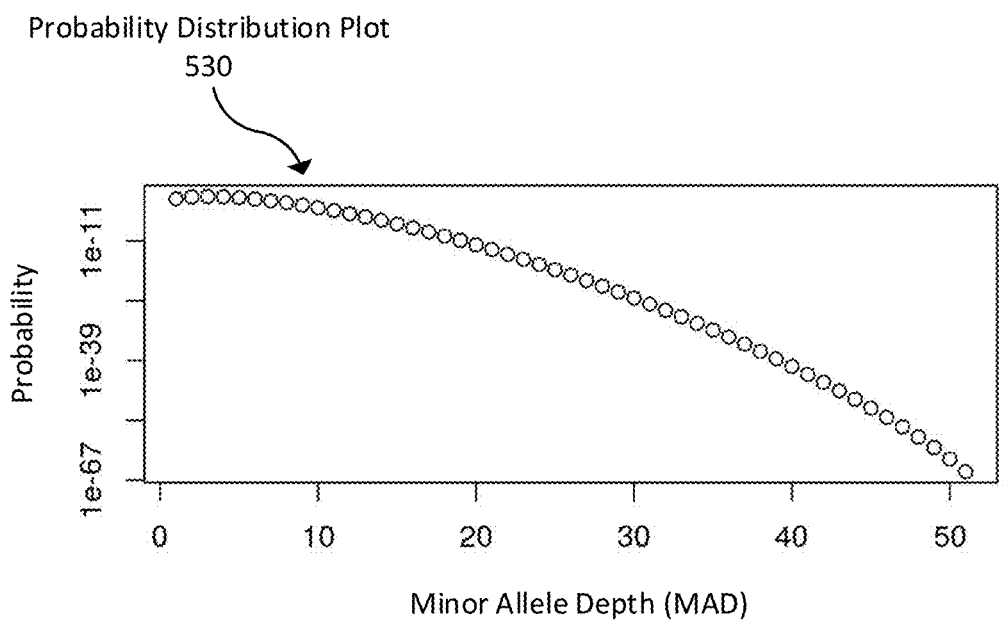
Figure 5D:
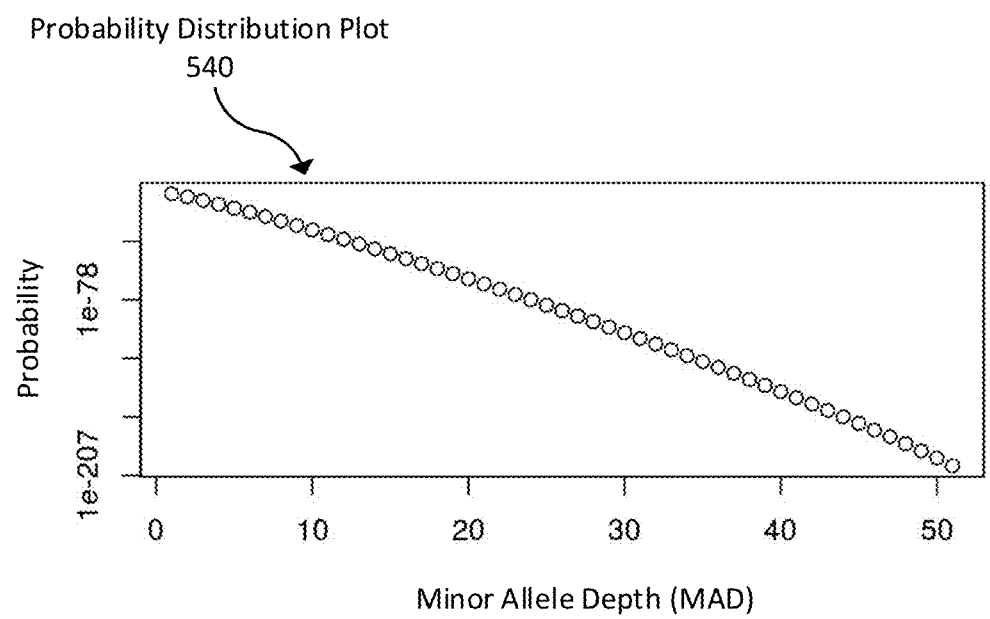
Figure 5E:
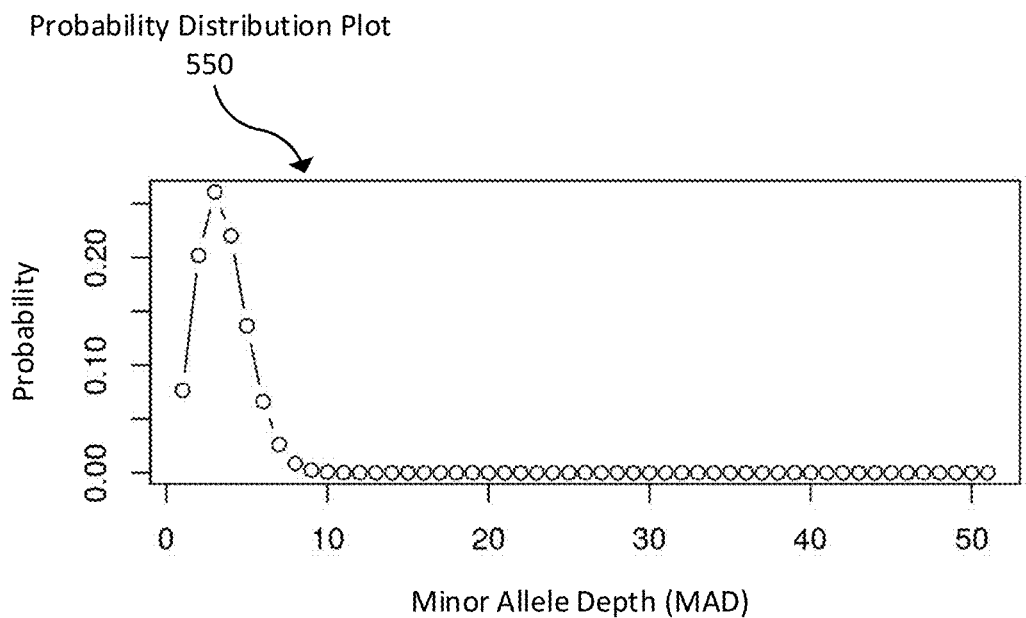
Figure 5F:
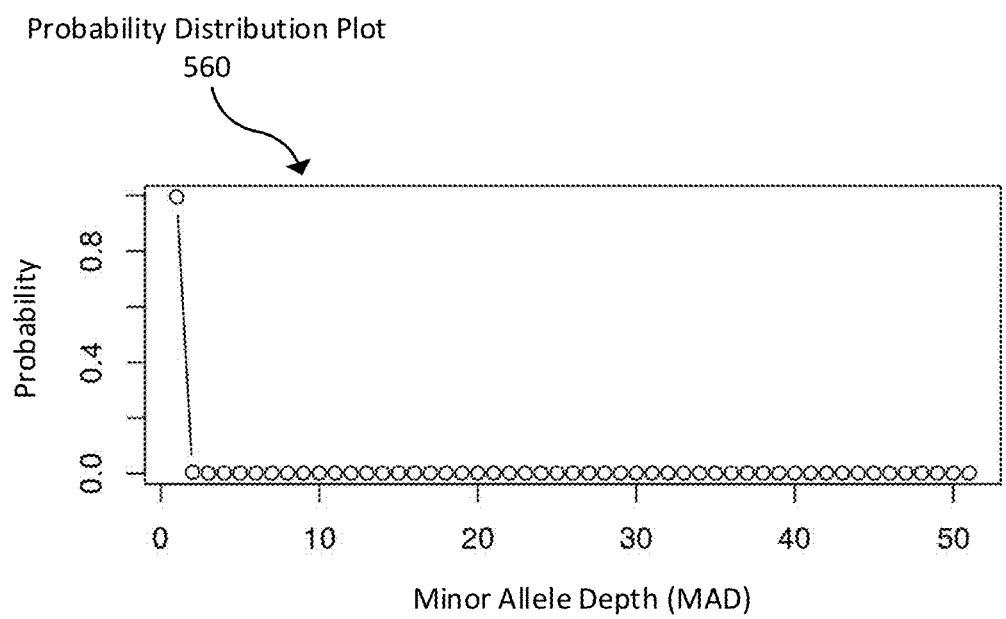

FIG. 5B-FIG. 5F are probability distribution plots for different contamination levels $\alpha$ and mutation probabilities ε. FIG. 5B is a probability distribution plot 520 for a test sample with a contamination level $\alpha$ of 0% and a probability of observing a specific mutation ε of 0.01%. FIG. 5C is a probability distribution plot 530 for a test sample with a contamination level α of 10% with a logarithmically scaled y axis. FIG. 5D is a probability distribution plot 540 for a test sample with a contamination level α of 0% and a probability of observing a specific mutation & of 0.01% with a logarithmically scaled y-axis. FIG. 5E is a probability distribution plot 550 for a test sample with a contamination level α of 10% and a blackswan value of 0.002 (a minimum contribution level of 0.002). FIG. 5F is a probability distribution plot 560 for a test sample with a contamination level α of 0%, a probability of observing a specific mutation of 0.01% and a blackswan value of 0.002.

The generic site specific model can be simplified using prior probabilities of contamination. The simplified model can be represented as:

$$P(D|\alpha)=P_C \cdot P(D|\alpha,C)+(1-P_C)P(D|\alpha=0,!C) \qquad (6)$$

where $P_C$ is the probability of contamination of the test sample based on a prior observation of a contaminant with a genotype different from the host genotype C, $P(D|\alpha,C)$ is the probability of observing the data D with a contamination level α given the SNP is contaminated, $(1-P_c)$ is the probability of no contamination and $P(D|\alpha=0,!C)$ is the probability of observing data D with a contamination level α of 0% (i.e., no contamination, denoted as !C).

Alternatively stated, $P_C$ is the probability that an SNP at a site is contaminated with a contaminant of a different allele type than the host given a contamination level α. In one example, the simplified model determines the prior probability of contamination $P_C$ using the following:

$$P_C = \begin{cases} 1-(1-MAF)^2 & \text{if host is } A/A \\ 1-MAF^2 & \text{if host is } B/B \end{cases}$$

where MAF is the minor allele frequency, A/A is a homozygous reference allele, and B/B is an homozygous alternative allele. Here, heterozygous alleles are removed and are not considered in determining the probability of contamination for a test sample.

V.B Probability of Contamination for a Sample

As previously described, in one embodiment, the contamination detection workflow 400 uses a likelihood model to determine contamination in a sample. Here, to determine contamination in a sample, the likelihood model determines a level of contamination a that maximizes a likelihood function L (a). The likelihood function L (a) can be written as:

$$L(\alpha) \propto P(D|\alpha) = \Pi_{i=1}^N \max(P(D_i|\alpha),\beta) \qquad (3)$$

where $P(D|\alpha)$ is the probability of observing data D given contamination level α, β is a minimum allowable probability, N is the number of homozygous (A\A or B\B) SNPs of the sample, and $D_i$ is the observed data for a given SNP.

The likelihood function L (a) is proportional to the probability of observing data D given a contamination level α ($P(D|\alpha)$). The probability of the data D given a contamination level α takes into account all SNPs of the sample. That is, L (a) is the product over each SNP in the sample of the maximum of the probability of the data in that SNP given the contamination level α ($P(D_i|\alpha)$). For each SNP, if the probability of the data D given a contamination level α is below a threshold, the probability for that SNP can be assigned a value β. The value β is a minimum probability that is set as a black swan term (e.g., $\beta=3.3\times10^{-7}$) which limits the lowest value each SNP evaluated can contribute to the likelihood function L (a). The probability of contamination at of a single SNP site ($P(D_i|\alpha)$) is described in more detail in Section V.A.

V.C Probability of Contamination for a Sample Using Likelihood Tests

In one example of determining the likelihood of contamination, the contamination detection workflow 400 applies a likelihood model including two separate likelihoods tests.

In the first likelihood test, the product term of the likelihood function L (a) is used to calculate a first likelihood ratio (LR) representing the maximum contamination likelihood that is obtained from testing a series of contamination levels $\alpha_i$ against the minor allele frequency in a sample. That is, which level of contamination a gives the highest contamination likelihood.

The first likelihood ratio $LR_1$ uses a first null hypothesis that the sample is contaminated at a maximum of a series of contamination levels α ($L(\alpha=\alpha_i)$) based on the MAF of the observed SNPs. That is, the sample is contaminated at a contamination level $\alpha_{max}$ giving the highest likelihood of contamination. Therefore, the first null hypothesis can be written as:

$$L_{max}=\max[L_1(\alpha=0.001),L_2(\alpha=0.002),\ldots L_i(\alpha=0.5)] \qquad (4)$$

The first likelihood ratio also uses a first hypothesis that there is no contamination in the sample ($L(\alpha=0.000)$). Therefore, the first likelihood ratio test $LR_1$ can be written as:

$$LR_1 = \frac{\max[L(\alpha=0.001), L(\alpha=0.002), L(\alpha=0.003) \ldots L(\alpha=5)]}{L(\alpha=0.000)} \qquad (5)$$

Generally, the first likelihood ratio $LR_1$ results in a value. The sample is considered to pass the first likelihood test if the value of the first likelihood ratio $LR_1$ is above a threshold level. That is, it is likely that the sample is contaminated at a contamination level α.

In the second likelihood test, the likelihood function L (a) is used to calculate a second likelihood ratio $LR_2$ representing a likelihood that observed minor allele frequencies are due to contamination rather than due to a constant increase in noise across all SNPs.

The second likelihood ratio $LR_2$ uses a second null hypothesis $L_{max}$ MAF that is the same as the first null hypotheses (Eqn. 4). Additionally, the second likelihood ratio $LR_2$ uses a second hypothesis $L_{noise}$ that a sample contaminated at contamination level $\alpha_{max}$ includes minor allele frequencies at an average allele frequency of previously observed SNPs (uniform (MAF)). The second null hypothesis can be written as:

$$L_{noise}=L(\alpha_{max}|\text{uniform}(MAF)) \qquad (6)$$

Accordingly, the second likelihood ratio can be written as:

$$LR_2 = \frac{L_{max}}{L_{noise}} = \frac{\max[L_1(\alpha=0.001), L_2(\alpha=0.002), \ldots L_i(\alpha=.5)]}{L(\alpha_{max}|\text{uniform}(mAF))} \qquad (7)$$

The second likelihood ratio $LR_2$ results in a value. The sample is considered to pass the second likelihood test $LR_2$ if the value is above a threshold. That is, it is likely that the observed MAF is due to contamination and not due to noise. Alternatively stated, the second likelihood test passes when a specific arrangement of previously observed MAFs are significant in determining the contamination likelihood, while a random distribution of previously observed MAFs are insignificant in determining contamination likelihood.

If a test sample passes both of the likelihood tests, then the sample is called as contaminated at contamination level α which passes the tests. If a test sample fails either of the likelihood tests, then it is not called as contaminated.

In other configurations, the contamination detection workflow can use additional or fewer likelihood tests to determine if a sample is contaminated.

V.D Determining a Contamination Source

In one example of determining the likelihood of contamination, the likelihood model of the contamination detection workflow 400 can additionally determine a likely source of contamination. Detecting the source of contamination enables the assessment of risk introduced by the contaminant, as well as the point in sample process in which it happened, such as, for example, any step of process 100 or 300. In contamination detection workflow 400, the genotypes of likely contaminants may be used in place of prior probabilities from population SNPs. Introduction of prior probabilities of contamination will either increase or decrease the likelihood ratio relative to the likelihood ratio obtained by for probabilities based on the population.

The likelihood model can be informed by the prior probabilities of SNPs from the known genotypes of samples that were processed in the same batch as the test sample (or a set of related batches). A likelihood test is then performed to determine if knowing the exact genotype probabilities gives a higher value than the likelihood obtained using the population MAF probability. If the difference is significant, it can be concluded that a given sample is the contaminant.

For a given SNP, three observed genotypes are possible: homozygous reference 0/0, heterozygous 0/1, and homozygous alternative 1/1, where 0 represents the reference allele and 1 the alternative allele. In a normal (uncontaminated) sample, the expected allele frequency values observed are expected to be close to 0, 0.5 and 1 for genotypes 0/0, 0/1 and 1/1, respectively. However, in a contaminated sample, the observed allele frequency values can be expected to shift from 0, 0.5, and 1, as the SNPs vary across the population, and thus, have a higher likelihood of being present in a contaminating sample.

V.E Contamination Detection Using Likelihood Tests

It is important to be able to distinguish between contamination and noise. As noted above, processing system 200 can be used to detect contamination in a test sample. For example, using the contamination detection workflow 400 a contamination event can be detected based on a plurality (or set) of observed variant allele frequencies in a test sample. In one embodiment, the observed variant allele frequencies can be compared to population MAFs from a plurality of SNPs for the detection of cross-sample contamination.

Figure 6:
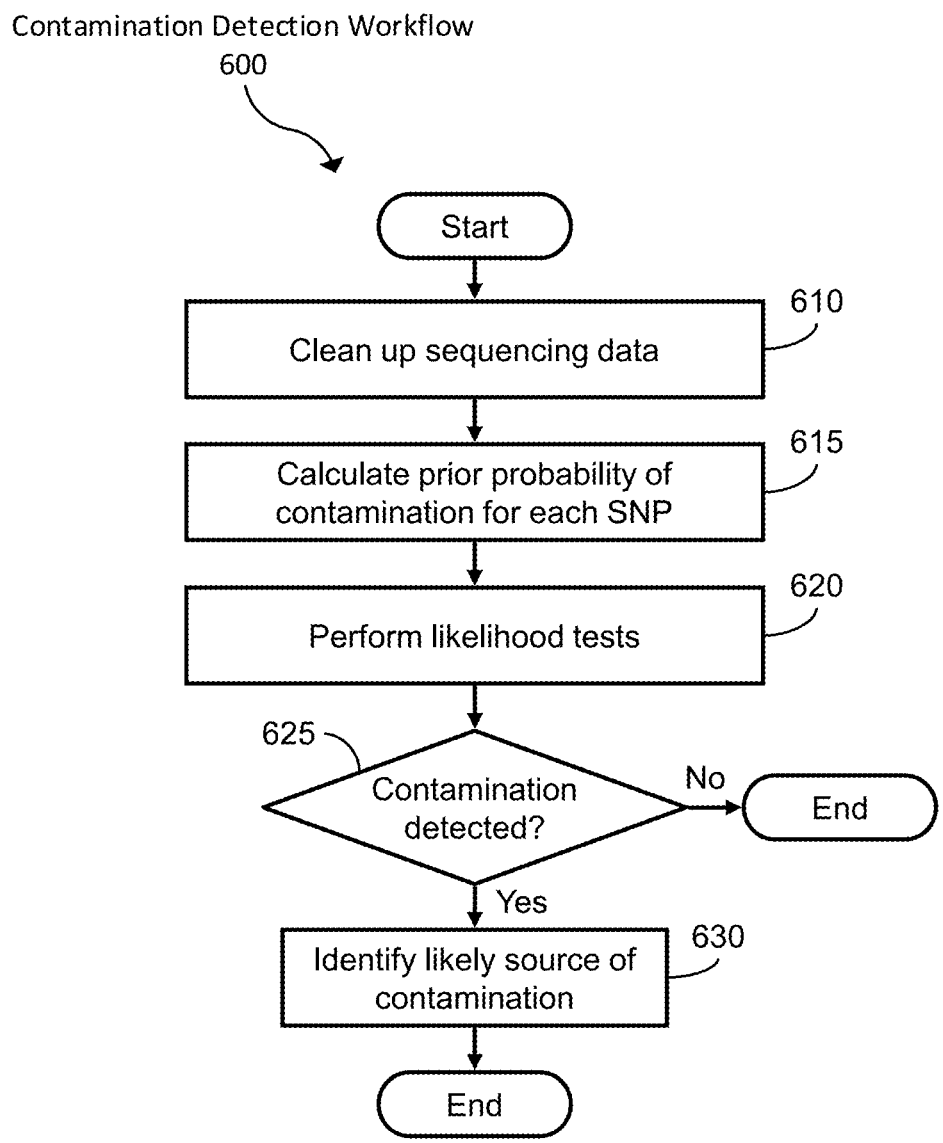
FIG. 6 illustrates a flow diagram of a workflow for detecting contamination of sequencing data, according to one example embodiment.

FIG. 6 illustrates a flow diagram illustrating a contamination detection workflow 600 performed in accordance the workflow 400 of FIG. 4. The detection workflow 600 of this embodiment includes, but is not limited to, the following steps.

At step 610, sequencing data obtained from a sample (e.g., using the process 300) is cleaned up and genotypes are neutralized. For example, data cleaning may include filtering out non-informative SNPs, removing SNPs with no coverage, removing SNPs with high error frequencies (e.g., >0.1%), removing SNPs with high variance, removing SNPs with a depth less than a threshold, removing any heterozygous SNPs, removing SNPs with low coverage, and removing any SNPs that have a high heterogeneity rate. In other examples, homozygous alternative SNPs with variant frequency 0.8 to 1.0 can be negated (e.g., variant frequency 0.95 becomes 0.05) in order to put all the variant frequency data in one scale that can be linearly compared to minor allele frequency values. Further, the MAF values can be negated based on a samples genotype.

At step 615, a prior probability of contamination is calculated for each SNP based on host sample's genotype and minor allele frequency as described in Section V.B At step 620, a likelihood model including a maximum likelihood estimation is applied to determined contamination based on the prior probability of contamination for the SNPs. The likelihood model includes a first and a second likelihood test as described in Section V.C.

At a decision step 625, it is determined whether the test sample is contaminated. If a test sample passes both likelihood tests, then the sample is contaminated and workflow 600 proceeds to a step 630. If a test sample does not pass both likelihood tests, then the sample is not contaminated and workflow 600 ends.

At step 630, a likely source of contamination is identified based on the prior probabilities of SNPs from known genotypes of other samples that were processed in the same batch as the test sample (or a set of related batches) as described in Section V.D.

Figure 7:
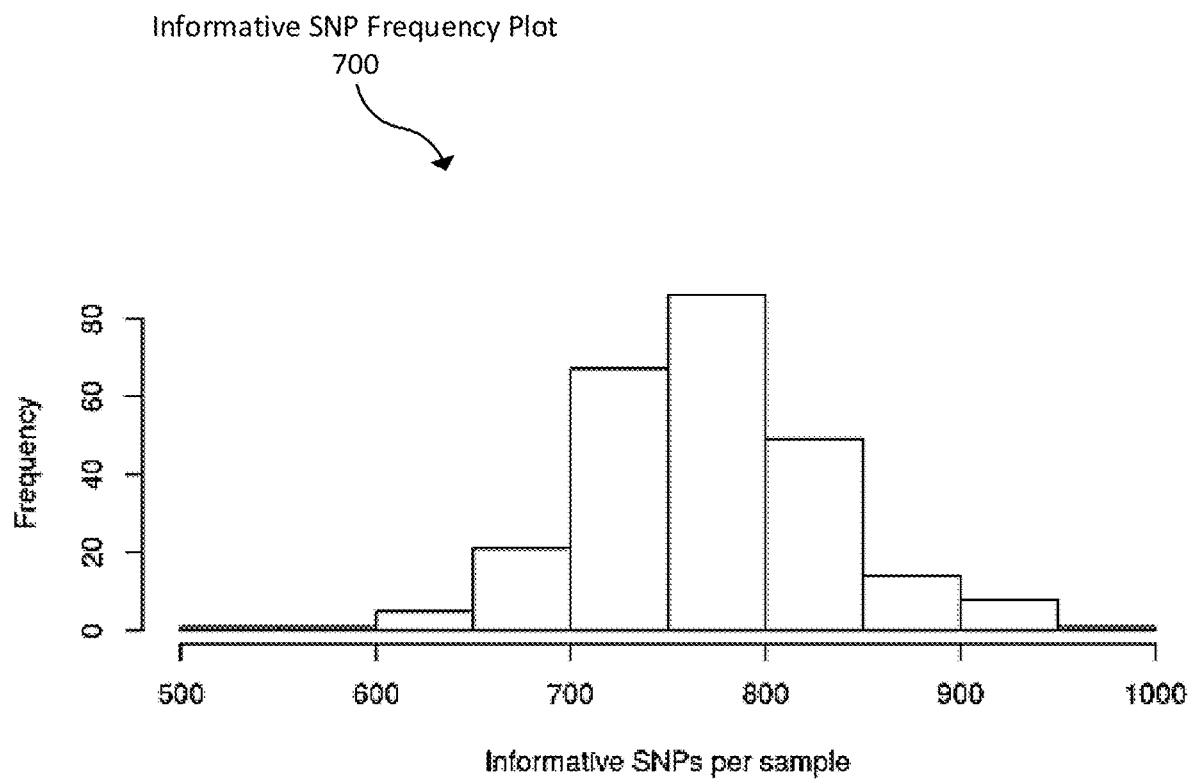
FIG. 7 is a plot showing the number of informative SNPs for a given sample pair for a contamination event, according to one example embodiment.

FIG. 7 is an informative SNP frequency plot 700 showing an example number of informative SNPs for a given sample pair for a contamination event. In an example set of 12174 SNPs, about 700 SNPs are informative SNPs. That is, for example, the SNPs are homozygous in the host and a different genotype in the contaminant.

Figure 8:
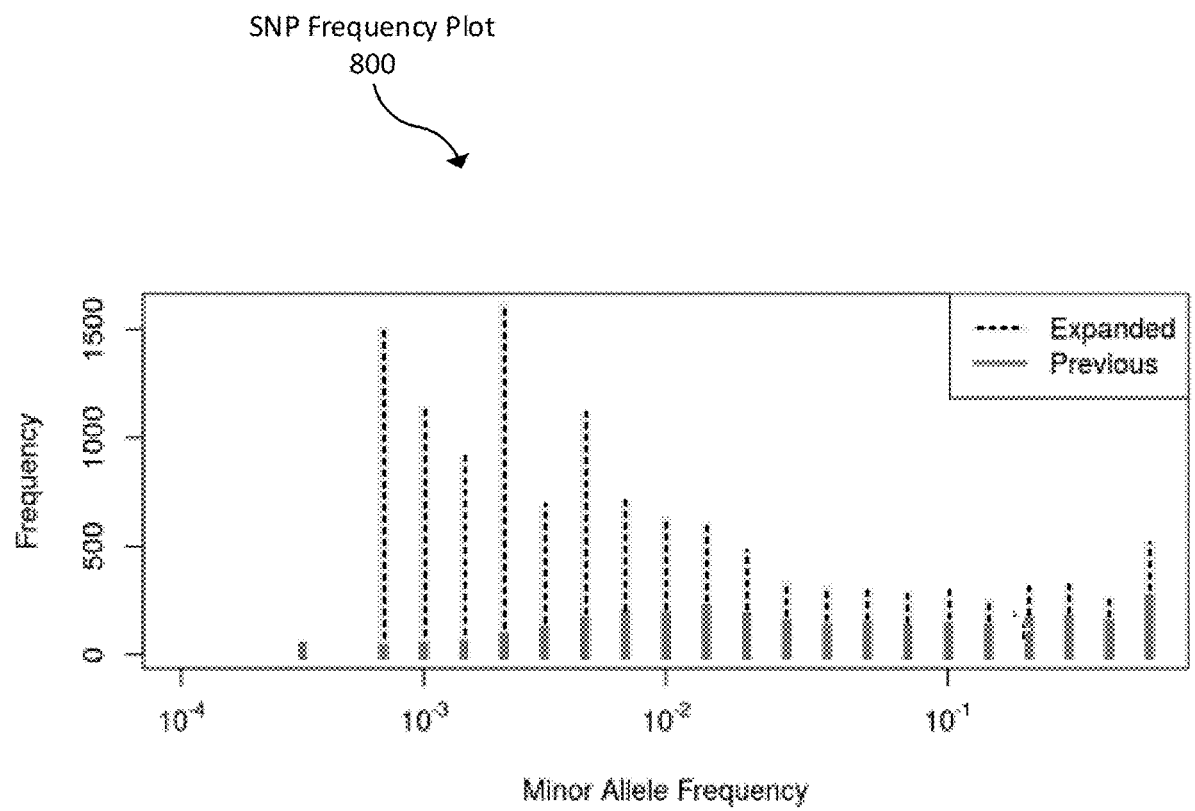
FIG. 8 is a plot showing the number of SNPs for each frequency bin for a first SNP set comprising 2718 SNPs and for a second SNP set comprising 12174 SNPs, according to one example embodiment.

FIG. 8 is an SNP frequency plot 800 showing the number of SNPs for each frequency bin for a first SNP set comprising 2718 SNPs ("Previous", indicated by solid lines) and for a second SNP set comprising 12174 SNPs ("Expanded", indicated by dashed lines). The minor allele frequencies for this SNP set range from about 10-3 to about 1. The data show that most of the SNPs in the SNP set are in the lower frequency range.

Figure 9:
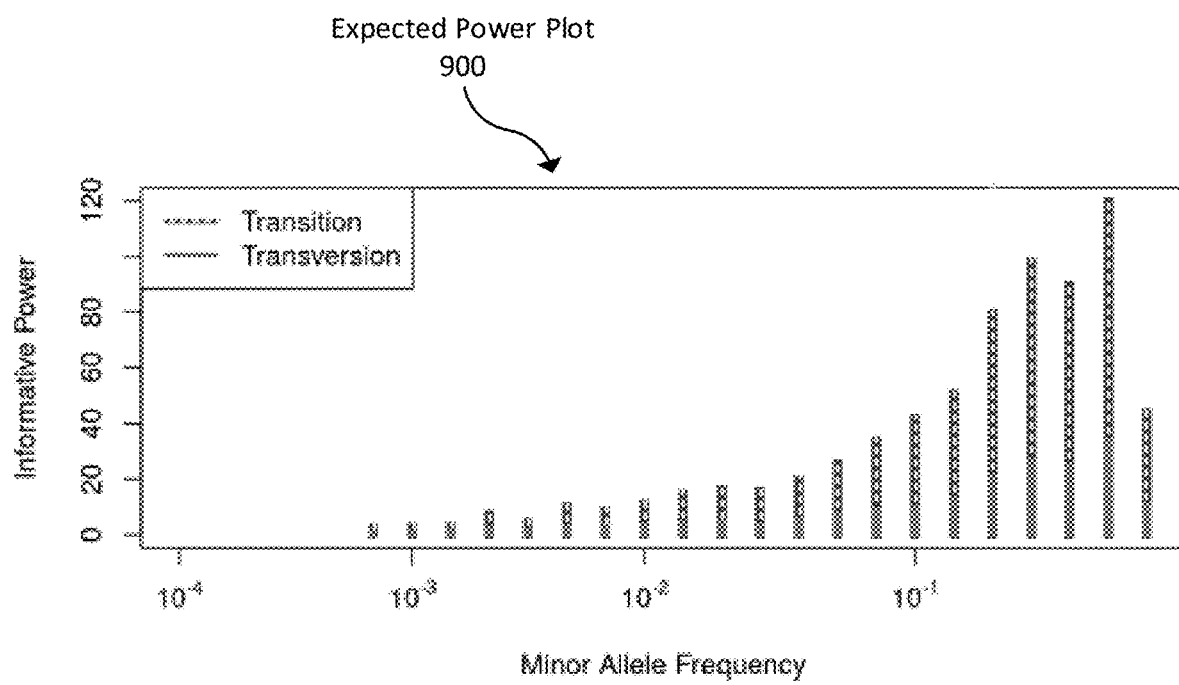
FIG. 9 is a plot showing the expected power of informative SNPs based on population minor allele frequency (MAF), according to one example embodiment.

FIG. 9 is an expected power plot 900 showing the expected power of informative SNPs based on population minor allele frequency (MAF). The expected power is: Power=$n \times ((1-p)^2 \times (1-(1-p)^2 + p^2 \times (1-p^2)$, where p is the MAF and n is the number of SNPs in a MAF bin. The data show that the highest power is for SNPs with higher MAFs. Transitions (dashed lines) correspond to substitutions that are between purine bases (A, G) or between pyrimidine bases (C, T), whereas transversions (solid lines) are interchanges of purine and pyrimidine bases.

VI. Limit of Detection

To determine the limit of detection (LOD) of contamination detection workflow 400, two clean samples were mixed in silico at different contamination levels (ranging from 50% down to 0.01% contamination level α). Here, the limit of detection is considered to be the lowest contamination level at which the specificity is above 95%.

Figure 10:
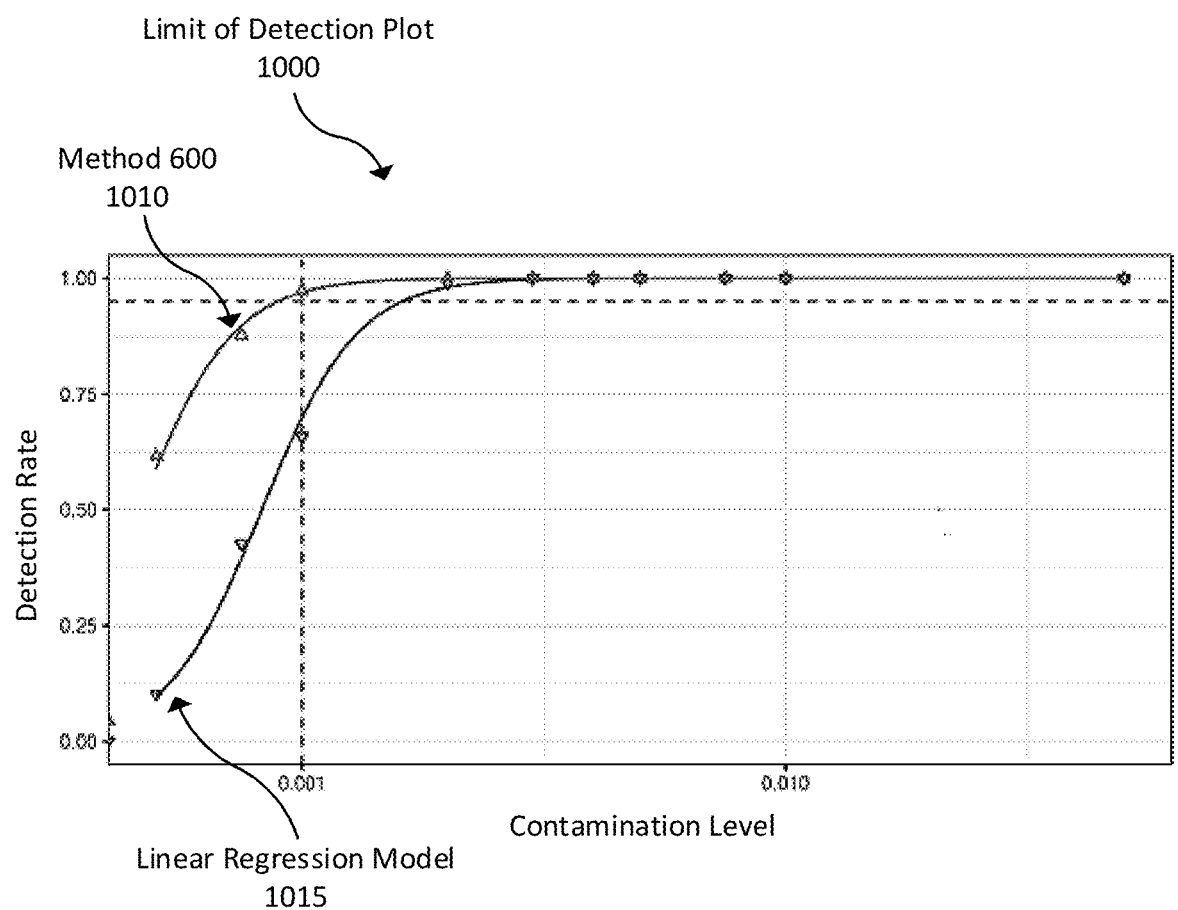
FIG. 10 is a plot showing the limit of contamination detection obtained using the contamination detection application, according to one example embodiment.

FIG. 10 is a limit of detection plot 1000 showing the limit of contamination detection obtained using detection workflow 400 (e.g., workflow 600). In plot 1000 the x-axis is the contamination level and the y-axis is the detection rate. Limit of detection for detection workflow 400 was compared against the limit of detection for a robust linear regression model for contamination detection (see, e.g., U.S. Patent Appl. No. 62/460,268, entitled "Detecting cross contamination in sequencing data"). Plot 1000 shows a line 1010 of the detection rate obtained using contamination detection workflow 600. The LOD using contamination detection workflow 500 is about 0.1% contamination level. Plot 1000 also shows a line 1015 of the detection rate obtained using the robust linear regression model. The LOD using the linear regression model is about 0.2% contamination level.

VII. Contamination Detection Validation

Figure 11:
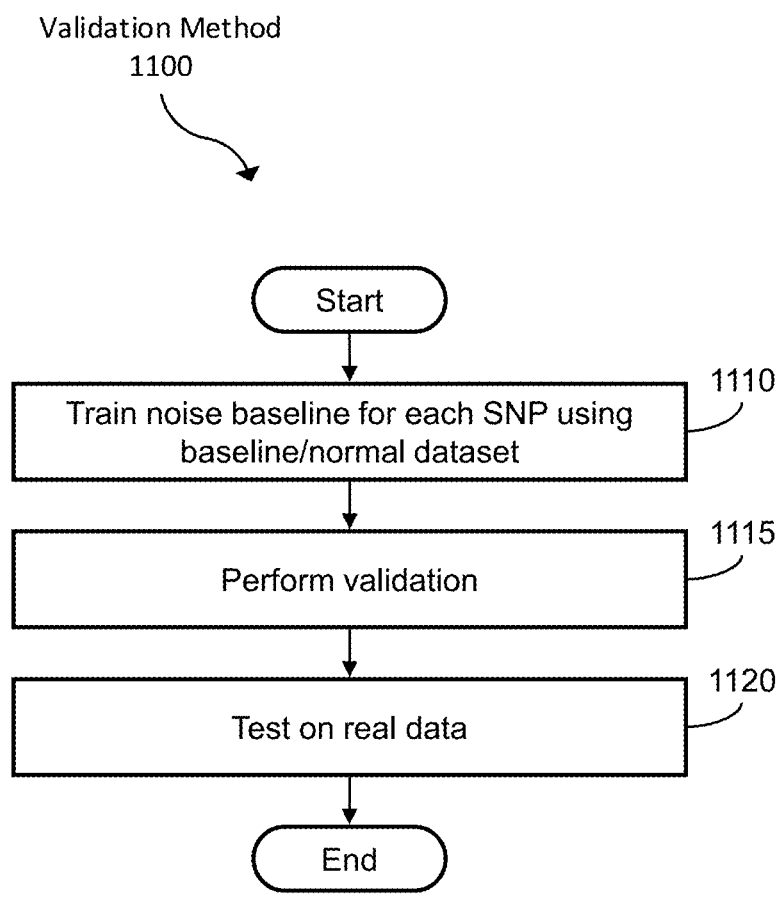
FIG. 11 illustrates a workflow of a method of validating the contamination detection application, according to one embodiment, according to one example embodiment.

Detection workflow 400 was validated using a three-step process. FIG. 11 illustrates an example of a method 1100 for validating contamination detection workflow 400 (e.g., workflow 600). Validation method 1100 may include, but is not limited to, the following steps.

At a step 1110, a background noise baseline for each SNP is generated using a set of normal training samples (e.g., 80 normal, uncontaminated samples). The noise baseline provides an estimate of the expected noise for each SNP and is used to distinguish a contamination event from a background noise signal. Generation of a noise (contamination) baseline is described in more detail with reference to FIG. 19.

At a step 1115, a 5-fold cross-validation process is performed. For example, datasets of 24 normal samples and in silico titrations are partitioned into a validation set and a training set. Here, the contamination levels ranges from 0.05% to 50%. The training set is used to train detection workflow 400 and set a threshold for calling a contamination event versus normal background noise. That is, detection workflow 400 can include a different threshold for each threshold and repeat of an SNP. The threshold is then tested on the validation set. This process is repeated a total of 10 times to identify a final threshold and LOD for calling a contamination event.

At a step 1120, the final threshold and LOD are tested on a real dataset (e.g., a cfDNA dataset from cancer patient samples).

Figure 12:
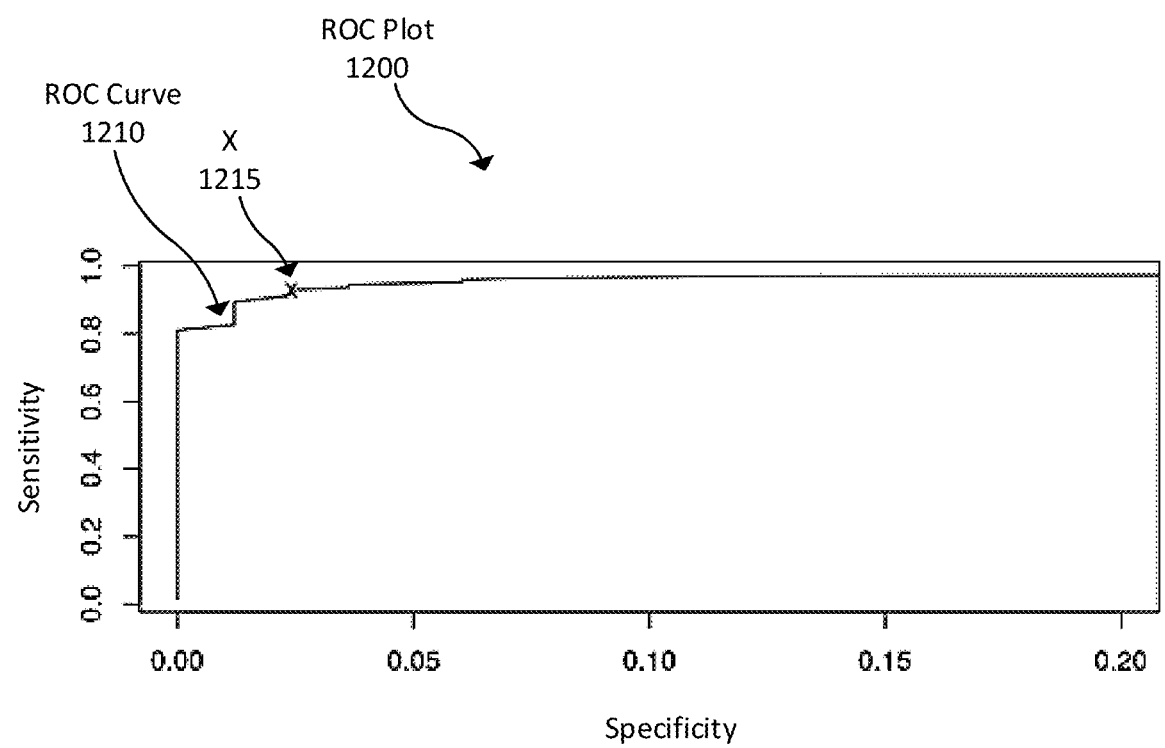
FIG. 12 is a plot showing an example of a ROC curve generated during cross-validation for threshold evaluation, according to one example embodiment.
Figure 13:
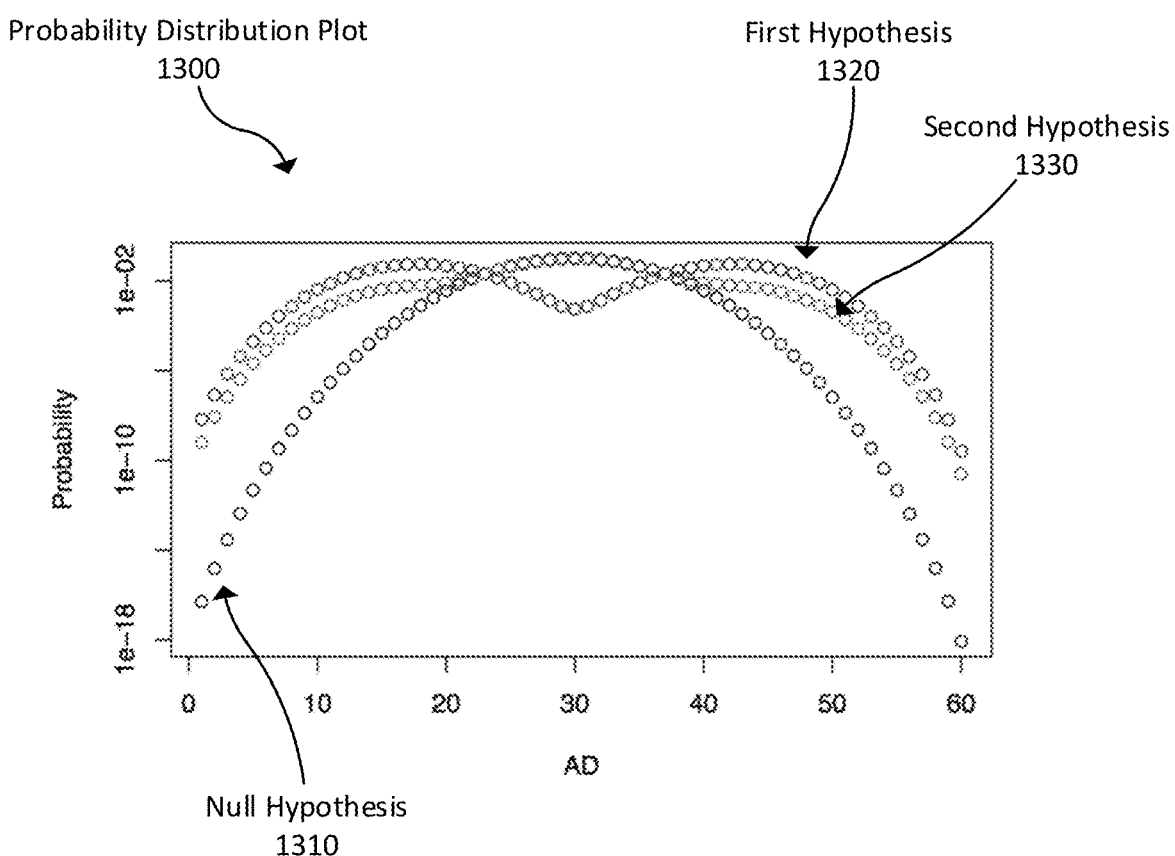
FIG. 13 is a plot showing the probability distributions for the three hypotheses of the loss of heterozygosity likelihood test, according to one example embodiment.

FIG. 12 is a receiver operating characteristic (ROC) plot 1200 showing an example of a ROC curve 1210 generated during cross-validation for threshold evaluation. In plot 1200 the x-axis is the specificity and the y-axis is the sensitivity. The "x" 1215 on ROC curve 1210 indicates the sensitivity and specificity level observed when the optimal threshold was applied. In this example, the optimal threshold (that has specificity above 95% and highest sensitivity) was 70 and the target specificity level was 0.97.

VIII. Loss of Heterozygosity in a Sample

Loss of heterozygosity (LOH) is an event that occurs in DNA which results in the gain or loss of a piece or whole chromosome, while the other chromosome stays intact, causing a loss of allelic balance at heterozygous sites. In some cases, the chromosome does not stay intact but still indicates LOH if the allelic balance is no longer 1:1. To explain in more simple terms, human DNA contains two copies of the genome, one from each chromosome pair. For the majority of positions in the genome, the base present in each copy is consistent between chromosomes; however, a small percentage may contain different bases than the reference chromosome (e.g., a SNP). Generally, copies from a chromosome pair are balanced. However, in some cases, one chromosome pair's copy of a region can be gained or lost resulting in a region having less or extra copies of one of the chromosomes. When this balance between chromosomes is lost, the region is said to show loss of heterozygosity.

LOH is a common occurrence in cancer and can be used in early cancer detection. Due to the loss of a copy pair, LOH can be read as a homozygous state of an allele. However, LOH does not necessarily imply an actual homozygous state (which would require the presence of two identical alleles in the cell). In particular, LOH creates an allelic state between heterozygote and homozygote (when sequencing cancer samples mixed with normal samples. In this case, if the deviation from heterozygosity is high enough, the allele appears as a contaminated homozygote state for a likelihood model. Thus, LOH in samples can generate false positives in contamination detection workflows (e.g., workflows 400 and 500) based on allele frequency of homozygous SNPs. That is, homozygous SNPs that are an indicator of cancer (via LOH) can also be an indicator of sample contamination. Thus, it is advantageous to remove homozygous SNPs caused by LOH from a sample before executing a contamination detection workflow.

VIII.A Determining Loss of Heterozygosity in a Sample

In one embodiment, the contamination detection workflow 400 may also detect contamination including samples with loss of heterozygosity. When detecting contamination, the contamination detection workflow calculates the probability that SNPs of the sample indicate loss of heterozygosity and removes the detected SNPs from the sample.

To determine if SNPs of a sample contain loss of heterozygosity, the contamination detection workflow 400 can perform a LOH likelihood test. The LOH likelihood test determines a likelihood that SNPs of the sample are indicative of LOH rather than contamination. The LOH likelihood test includes a null hypothesis, a first hypothesis, and a second hypothesis.

The null hypothesis $H_0$ represents the probability of observing a minor allele depth (MAD) and total depth (DP), indicating no loss of heterozygosity with heterozygosity level $\gamma$ (P(MAD|DP, $\gamma$)). That is, the null hypothesis $H_0$ indicates the probability that the observed number of minor alleles indicate heterozygosity. Generally, the heterozygosity level $\gamma$ is 0.5 but can be any other value. Here, the heterozygosity level is the ration of reference alleles when the chromosomes are balanced. In one configuration, the probability of observing a minor allele depth indicating no LOH can be represented by a binomial distribution based on the MAD, DP, and heterozygosity level $\gamma$. Thus, the null hypothesis $H_0$ can be written as:

$$H_0 = P(MAD|DP,\gamma) = \text{dbinom}(MAD,DP,\gamma) \quad (8)$$

where MAD is the minor allele depth, DP is the total depth (of both major and minor alleles, or "population"), $\gamma$ is the heterozygosity level, and dbinom is a binomial distribution function.

The first hypothesis $H_1$ represents the probability of observing a minor allele depth (MAD) indicating a LOH at a loss of heterozygosity level $\Delta$. That is, the first hypothesis $H_1$ illustrates the likelihood that the observed number of minor alleles indicate LOH at LOH level $\Delta$. In one example, $\Delta$ is a value determined empirically from estimations using the maximum likelihood models described herein. In one configuration, the probability of observing a minor allele depth indicating LOH can be represented by a binomial distribution based on the MAD, DP, the heterozygosity level $\gamma$, and a tested LOH level $\Delta$. Accordingly, the first hypothesis can be written as:

$$H_1 = P(MAD|DP,LOH_\Delta) = \text{dbinom}(MAD,DP,\gamma-\Delta) \quad (9)$$

where MAD is the minor allele depth, and DP is the total depth, $\gamma$ is the heterozygosity level, dbinom is a binomial distribution function, and $\Delta$ is a LOH level.

The second hypothesis $H_2$ represents the probability of observing a minor allele depth AD with a given contamination level $\alpha$ of the sample. That is, the second hypothesis $H_2$ gives the probability that the observed number of minor alleles indicate a contamination at level $\alpha$. In one configuration, the probability of observing a minor allele depth AD indicating a contamination at level $\alpha$ can be informed by the probability that the sample is contaminated based on the genotype of the contaminant (cP).

$$H_2 = (1-\alpha) \cdot P(AD|DP,\gamma) + \ldots \alpha((1-cP) \cdot P(AD|DP,\gamma) + cP \cdot P(AD|DP,LOH_\alpha)) \tag{10}$$

$$H_2 = P(AD|DP,\alpha) = (1-\alpha) \cdot H_0 + \alpha((1-cP) \cdot H_0 + cP \cdot H_1) \tag{11}$$

where AD is the minor allele depth, and DP is the total depth, $\gamma$ is the heterozygosity level, $\Delta$ is a LOH level, and cP is the contamination probability.

The LOH likelihood test $L_{LOH}$ compares the second hypothesis to the first hypothesis for each SNP of the population. For a given SNP, if the first hypothesis $H_1$ less the second hypothesis $H_2$ is above a threshold, then the SNP is removed from the population before determining if the sample is contaminated, otherwise, the SNP remains in the population. That is, if the SNP is more likely to include LOH than contamination, the SNP is removed from the population. The LOH likelihood test can be represented by the expression:

$$L_{LOH}(i) \to \begin{cases} \text{if } H_1 - H_2 \geq \varphi & \text{remove } SNP_i \\ \text{else} & \text{maintain } SNP_i \end{cases} \tag{12}$$

where $L_{LOH}$ (i) represents the LOH likelihood test taken for each SNP i, $H_2$ is the second hypothesis, $H_1$ is the first hypothesis, and $\varphi$ is a threshold value. In one example embodiment, threshold value q is determined from simulation tests for contamination detection but can be determined based on any other analysis. In some cases, the LOH likelihood test is performed for a set of SNPs representing large sections of chromosomes.

FIG. 12 shows a probability distribution plot 1300 of example probability distributions used for determining the LOH in a sample using the LOH likelihood test $L_{LOH}$. The x-axis is the allele depth for a sample and the y-axis is the determined probability for a hypothesis of the likelihood test $L_{LOH}$. The line 1310 shows the probability distribution of the null hypothesis that the sample does not include loss of heterozygosity or contamination. Alternatively stated, the line 1310 is the probability of observing a number of reads in the sample which indicate normal heterozygosity. The line 1320 represents the probability distribution of the first hypothesis $H_1$ that the sample includes loss of heterozygosity at a given LOH level $\Delta$. That is, the line 1320 represents the probability of observing a number of reads in the sample that include reads indicative of loss of heterozygosity in the sample. The line 1330 shows the probability distribution of the second hypothesis $H_2$ that the sample is contaminated at a contamination level $\alpha$ with contamination probability cP. That is, the line 1330 represents the probability of observing a number of reads in the sample that show contamination at a contamination level $\alpha$.

Figure 14A:
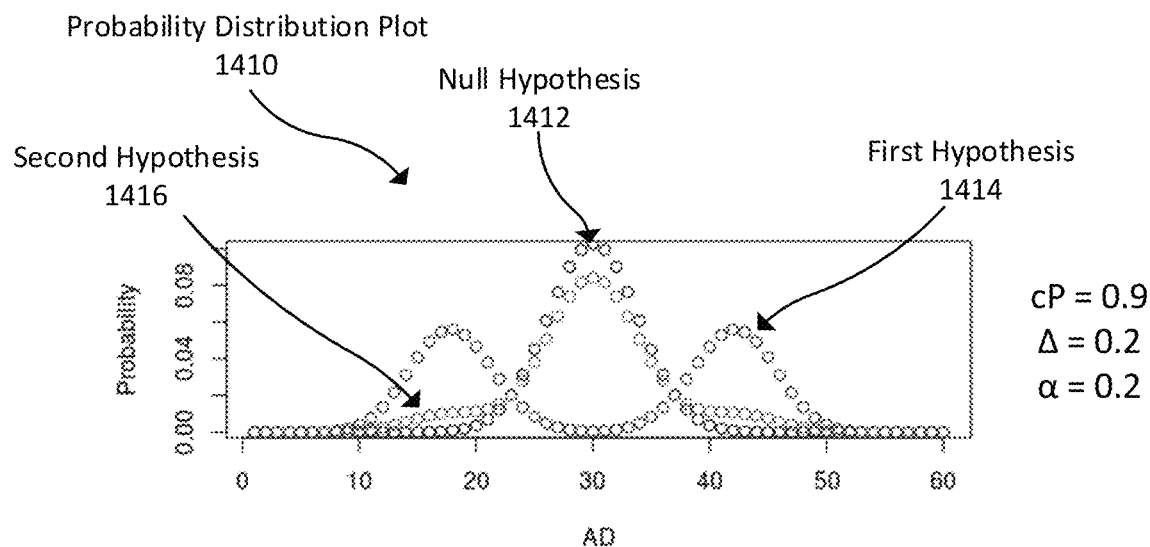
FIG. 14A is a plot showing the probability distributions for the three hypotheses of the loss of heterozygosity likelihood test for a sample with a high contamination probability, according to one example embodiment.
Figure 14B:
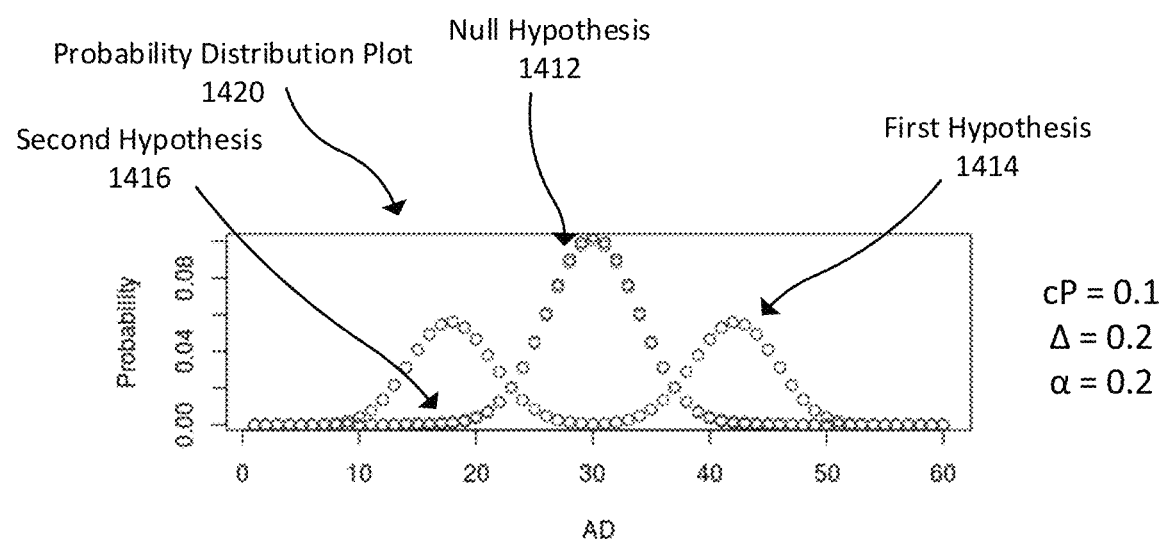
FIG. 14B is a plot showing the probability distributions for the three hypotheses of the loss of heterozygosity likelihood test for a sample with a low contamination probability, according to one example embodiment.

FIGS. 14A and 14B show probability distribution plots of the probability distributions for the null hypothesis $H_0$ (line 1412), the first hypothesis $H_1$ (line 1414), and the second hypothesis $H_2$ (red line 1416) using different values for the contamination probability cP, the loss of heterozygosity level $\Delta$, and contamination level $\alpha$. Plot 1410 shows the probability distributions with a contamination probability cP of 0.9, a LOH level $\Delta$ of 0.2, and a contamination level $\alpha$ of 0.2. Plot 1420 shows the probability distributions with a contamination probability cP of 0.1, a LOH level $\Delta$ of 0.2, and a contamination level $\alpha$ of 0.2. For each SNP of the sample, the LOH likelihood test $L_{LOH}$ compares the probability distributions for the first and second hypothesis. For SNPs of the sample with a difference between the LOH probability ($H_1$) and the contamination probability ($H_2$) above a threshold ($H_1$-$H_2 \geq \phi$), the LOH likelihood test $L_{LOH}$ can remove the likely LOH SNPs (or sequences including LOH SNPs) based on the analysis.

VIII.B Contamination Detection Using LOH Likelihood Tests

It is important to be able to distinguish between contamination and noise without calling false positives. Detection workflow 400 including workflow 1500 can include detecting LOH in the sample and filtering the samples including the LOH to improve the accuracy of contamination detection.

Figure 15:
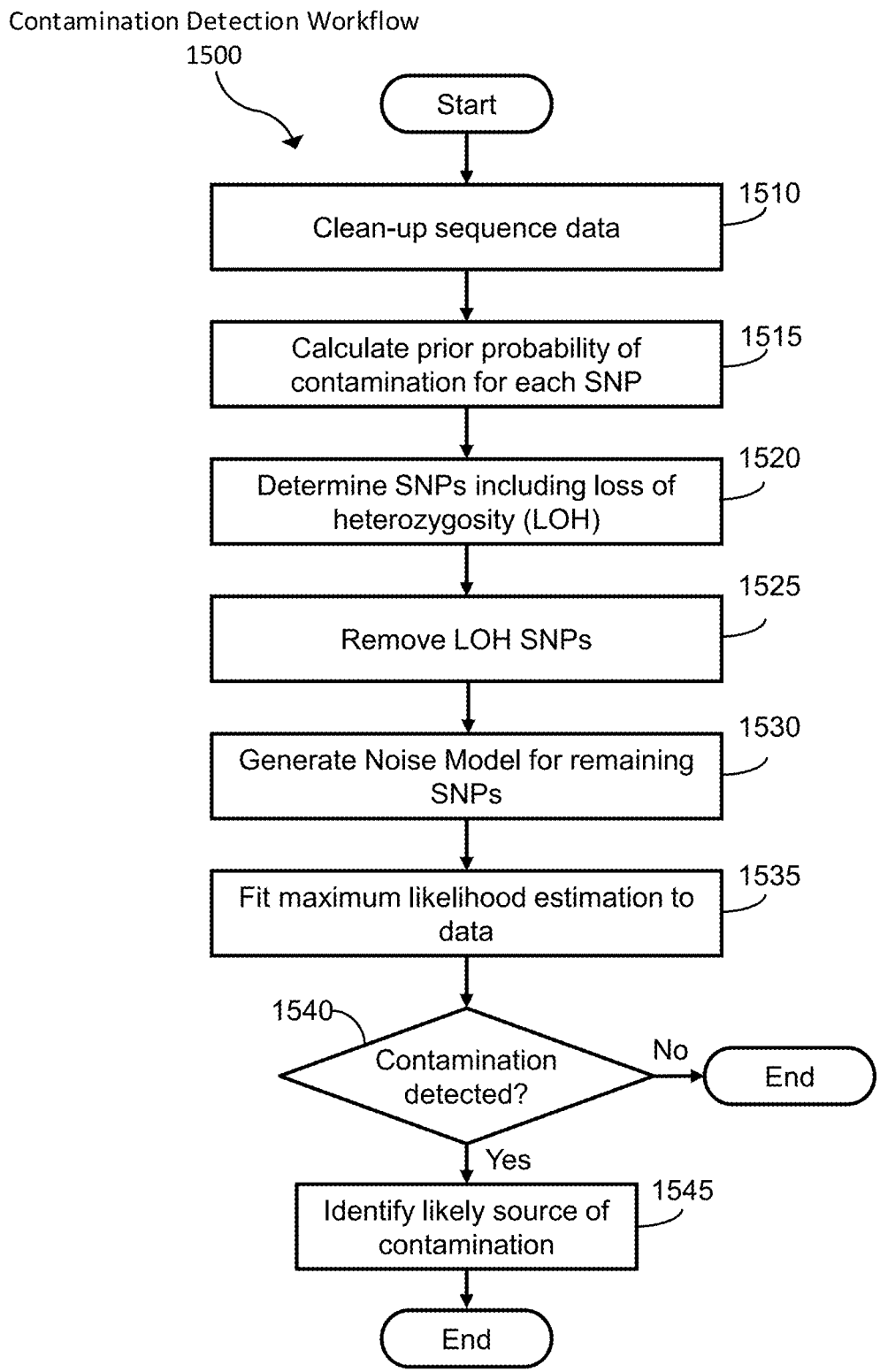
FIG. 15 illustrates a flow diagram of a method for removing sequencing data including loss of heterozygosity and detecting contamination in the remaining sequencing data, according to one example embodiment.

FIG. 15 illustrates a flow diagram of a workflow 1500 for detecting contamination performed in accordance with one embodiment. The contamination detection method of this embodiment includes, but is not limited to, the following steps.

At step 1510, the sequencing data is cleaned up and genotypes are normalized similarly to the clean-up 610 step of the workflow 600 in FIG. 6.

At step 1515, the workflow calculates a prior probability of contamination for each SNP based on the genotype of the contaminant similar to step 615 of FIG. 6.

At step 1520, a loss of heterozygosity likelihood test is performed to determine SNPs that include LOH. The LOH likelihood test is based on the LOH level $\Delta$, a contamination level $\alpha$, and a prior probability of contamination cP for the SNPs.

At step 1525, SNPs that are more likely to include loss of heterozygosity than contamination are removed from the population. In some cases, the difference in likelihood for each SNP is above a threshold level when removed.

At step 1530, a background noise model generates a background noise baseline calculated from a mean allele frequency of the SNPs across healthy samples. The background noise model generates a noise coefficient, which provides an estimate of the expected noise for each of the SNPs.

Following the generation of the noise model, the workflow 1500 proceeds similarly to the workflow 600 of FIG. 6. That is, detection workflow 1500 fits 1535 maximum likelihood estimation to data using likelihood tests, detects 1540 contamination, and identifies 1545 the likely source of contamination analogously to the corresponding steps of detection workflow 600.

Notably, these steps in workflow 1500 are performed using a population of SNPs in which sequences including LOH are removed. The resulting contamination detection 1540 achieves a higher specificity than the workflow 600 of FIG. 6.

IX. Validation of Contamination Detection with LOH Detection

IX.A In-Vitro Titration

Figure 16:
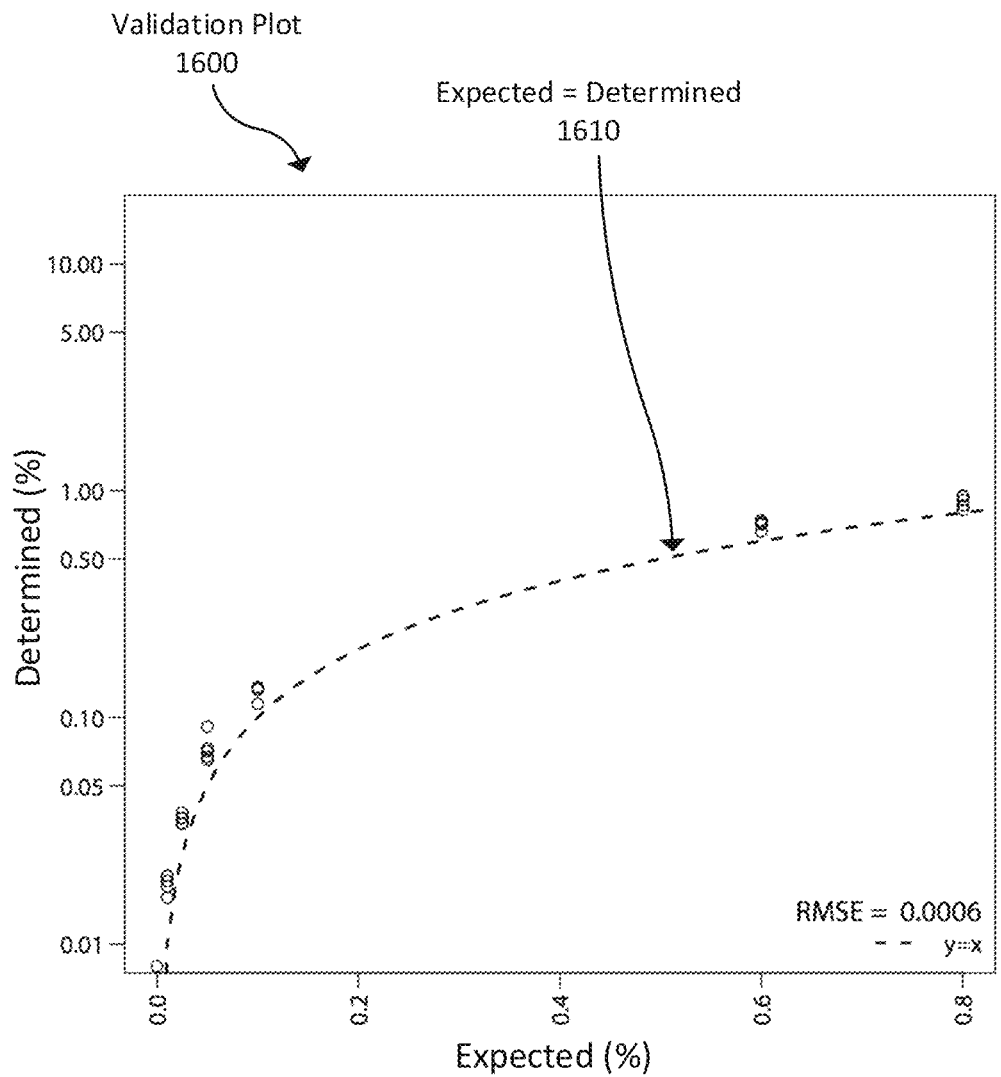
FIG. 16 is a plot showing the validation of the contamination detection including loss of heterozygosity removal via in-vitro titration experiments, according to one example embodiment.

FIG. 16 is a validation plot showing the validation of the detection workflow 1500. Here, in-vitro titration is used to introduce contamination to targeted sequences of 35 samples. Seven contamination levels (0.00%, 0.01%, 0.025%, 0.05%, 0.1%, 0.6% and 0.8%) are introduced into five samples each. The detection workflow 1500 is applied to the 35 samples to call contamination and determine the contamination level. The x-axis of the plot 1600 is the expected contamination level introduced to a sample via titration and the y-axis is the determined contamination level determined by a detection workflow. The dotted line 1610 on the plot 1600 indicates where the expected contamination level is equivalent to the detected contamination level. The data points on plot 1600 show the contamination levels determined by the detection workflow 1500. In this case the detection workflow 1500 called contamination with a specificity of 97.1% (in this example, 34/35). Error in the contamination detection was measured as 0.0006 using root mean square error.

Three alternate contamination workflows known in the art were used to measure the contamination in the samples. The three alternate workflows include: 1) "ContEst: estimating cross-contamination of human samples in next-generation sequencing data" from Cibulskis, K. et. al., *Bioinformatics*, 2011 (herein referred to as "ContEst"); 2) "Detecting and Estimating Contamination of Human DNA Samples in Sequencing and Array-Based Genotype Data" from Jun, G. et. al., *American Journal of Human Genetics*, 2012 (herein referred to as "VerifyBamID"); and 3) "Conpair: concordance and contamination estimator for matched tumor-normal pairs" from Bergmann, E. A. et. al., *Bioinformatics*, 2016 (herein referred to as "Conpair"). The RMSE errors for the three detection workflows were 0.001, 0.03, and 0.003, respectively.

Figure 17A:
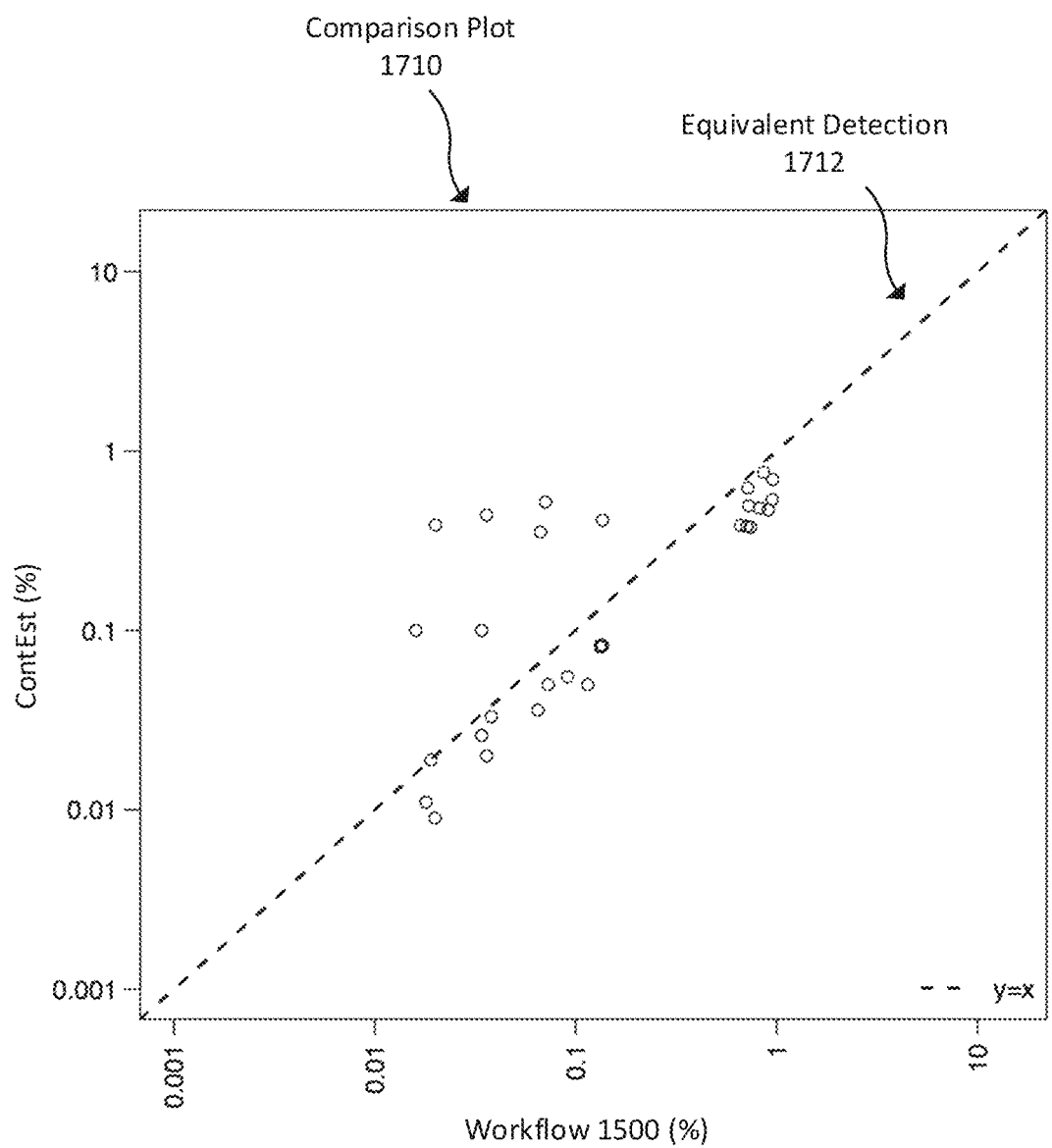
FIGS. 17A-17C are plots comparing the performance of methods for determining contamination detection including loss of heterozygosity removal to alternative detection methods known in the art for detecting contamination in samples contaminated via in-vitro titration, according to one example embodiment.
Figure 17B:
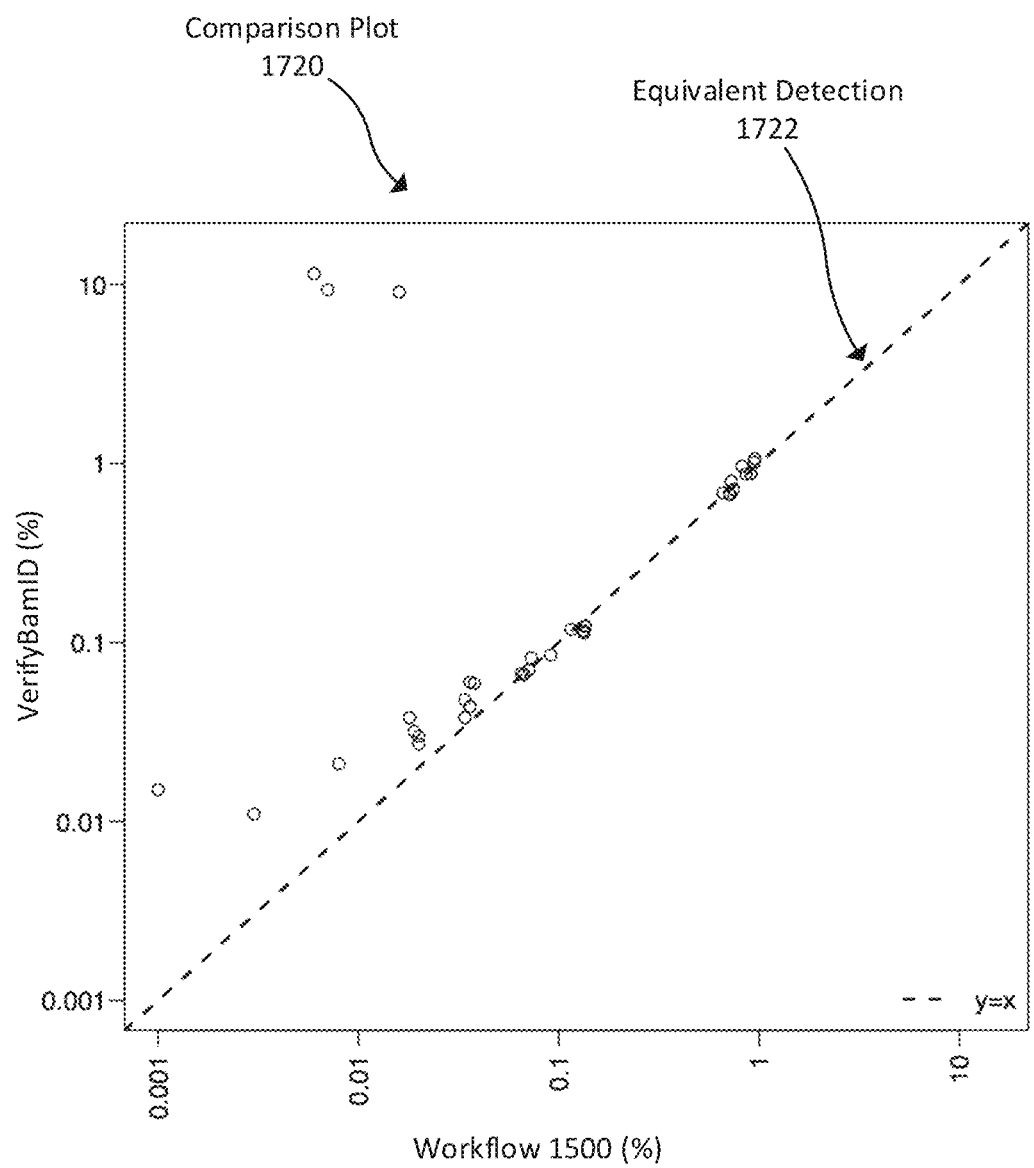
Figure 17C:
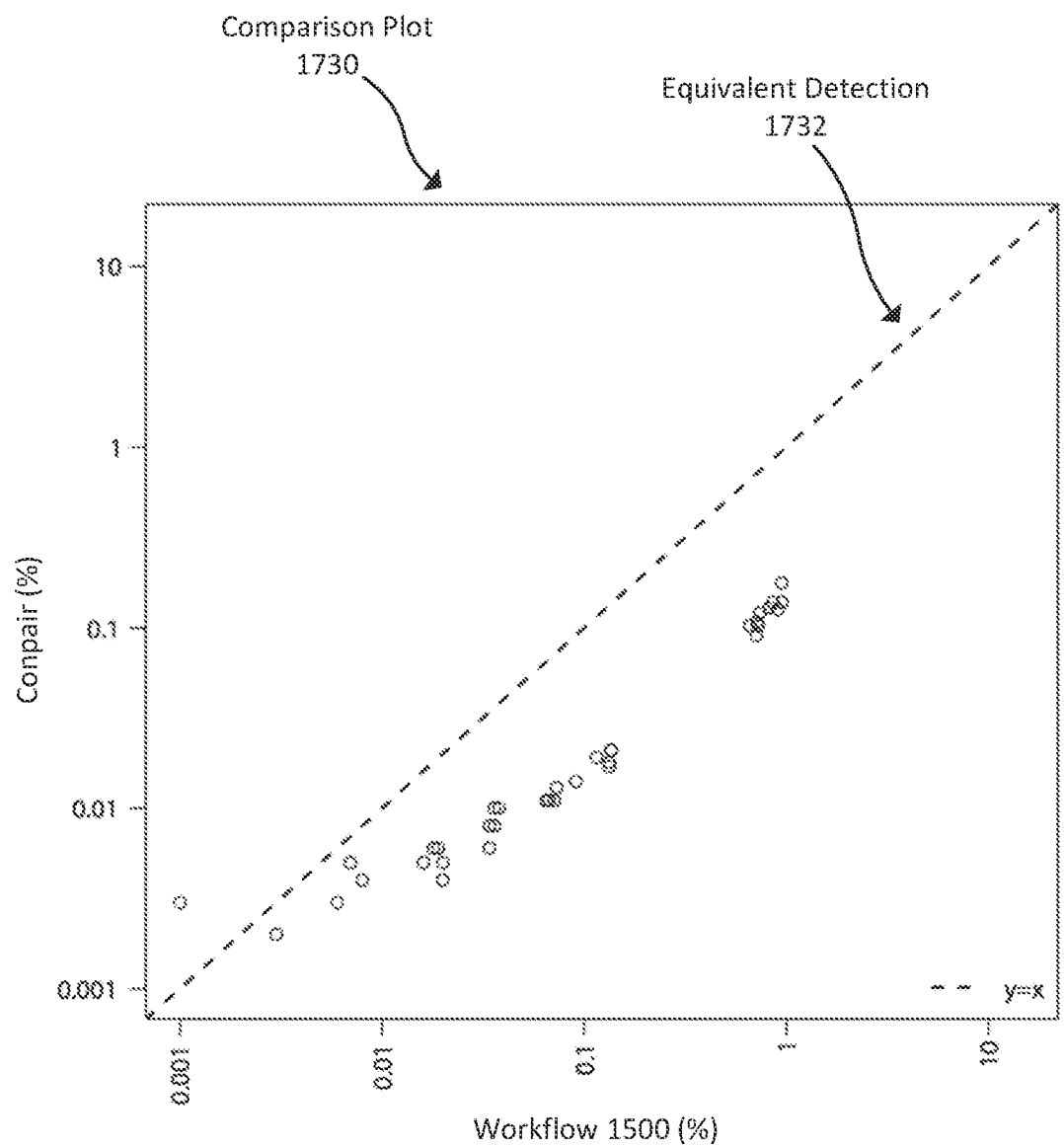

FIGS. 17A-17C are comparison plots illustrating the differences in the detected contamination level between workflow 1500 and the three alternate workflows 1-3. In FIGS. 17A-17C, the detected contamination level for workflow 1500 is the x-axis and the detected contamination level for the alternate workflow is the y-axis. The dotted line is a visual aid representing equivalent contamination detection between the workflow 1500 and the alternate workflow.

In plot 1710, the alternate workflow is ContEst. The plot 1710 illustrates that ContEst is not able to detect contamination below 0.01%. Line 1712 indicates where ContEst and contamination detection workflow 1500 detect contamination equally. Further, the error in detected contamination levels less than 0.5% is high. In plot 1720, the alternate workflow is VerifyBamID. Line 1722 indicates where VerifyBamID and contamination detection workflow 1500 detect contamination equally. The plot illustrates that VerifyBamID is not able to detect contamination below 0.01%. Further, contamination levels below 0.025% can sometimes call abnormally large contamination levels. In plot 1730, the alternate workflow is Conpair. Line 1732 indicates where Conpair and contamination detection workflow 1500 detect contamination equally. The plot 1730 illustrates that Conpair generally determines a contamination level lower than the contamination level determined by workflow 1500.

IX.B Non-Cancer Samples from 1000 Genomes Data

Figure 18A:
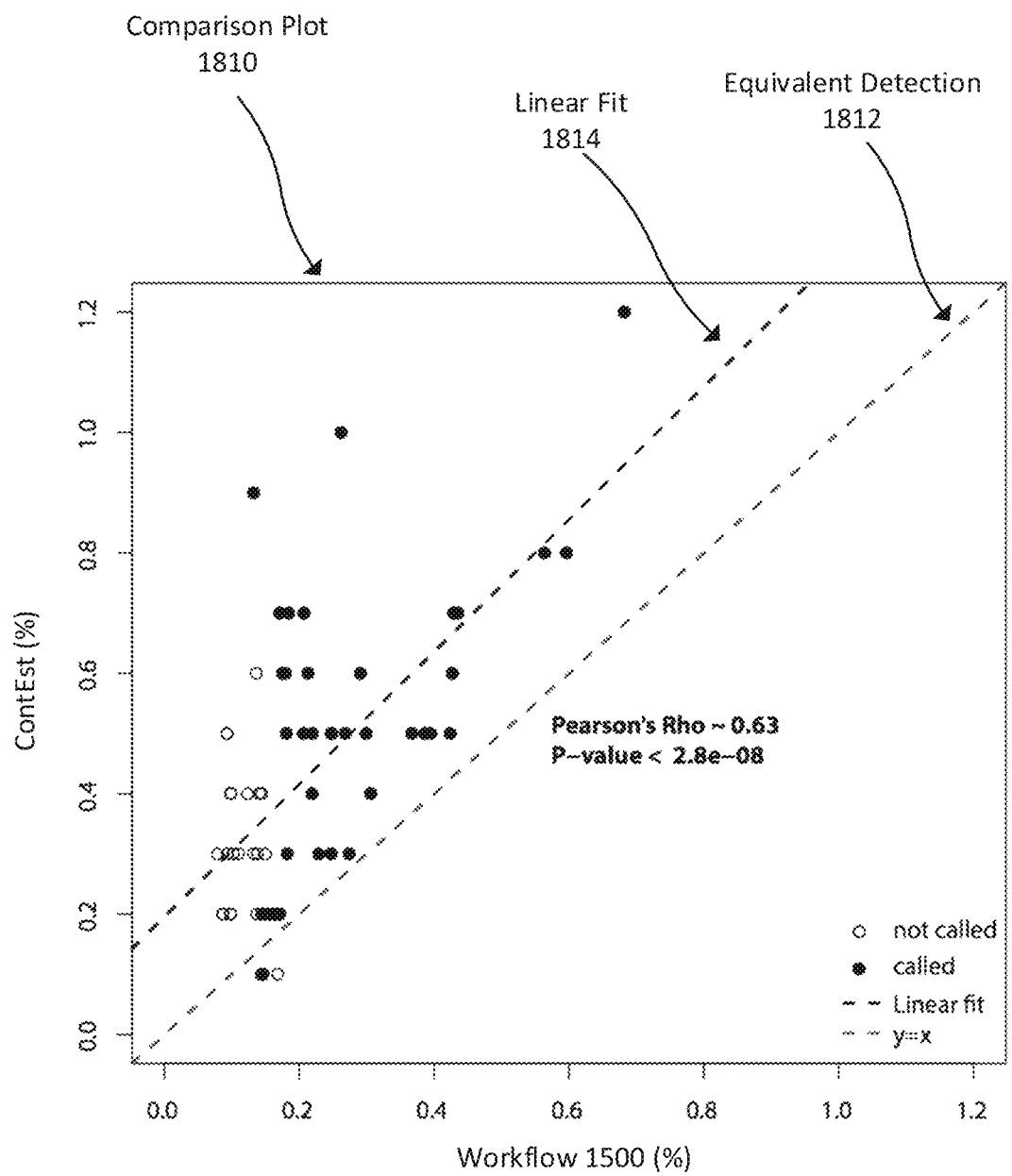
FIGS. 18A-18B are plots comparing the performance of contamination detection including loss of heterozygosity removal to alternative detection methods known in the art for detecting contamination in samples known to be cancer free, according to one example embodiment.
Figure 18B:
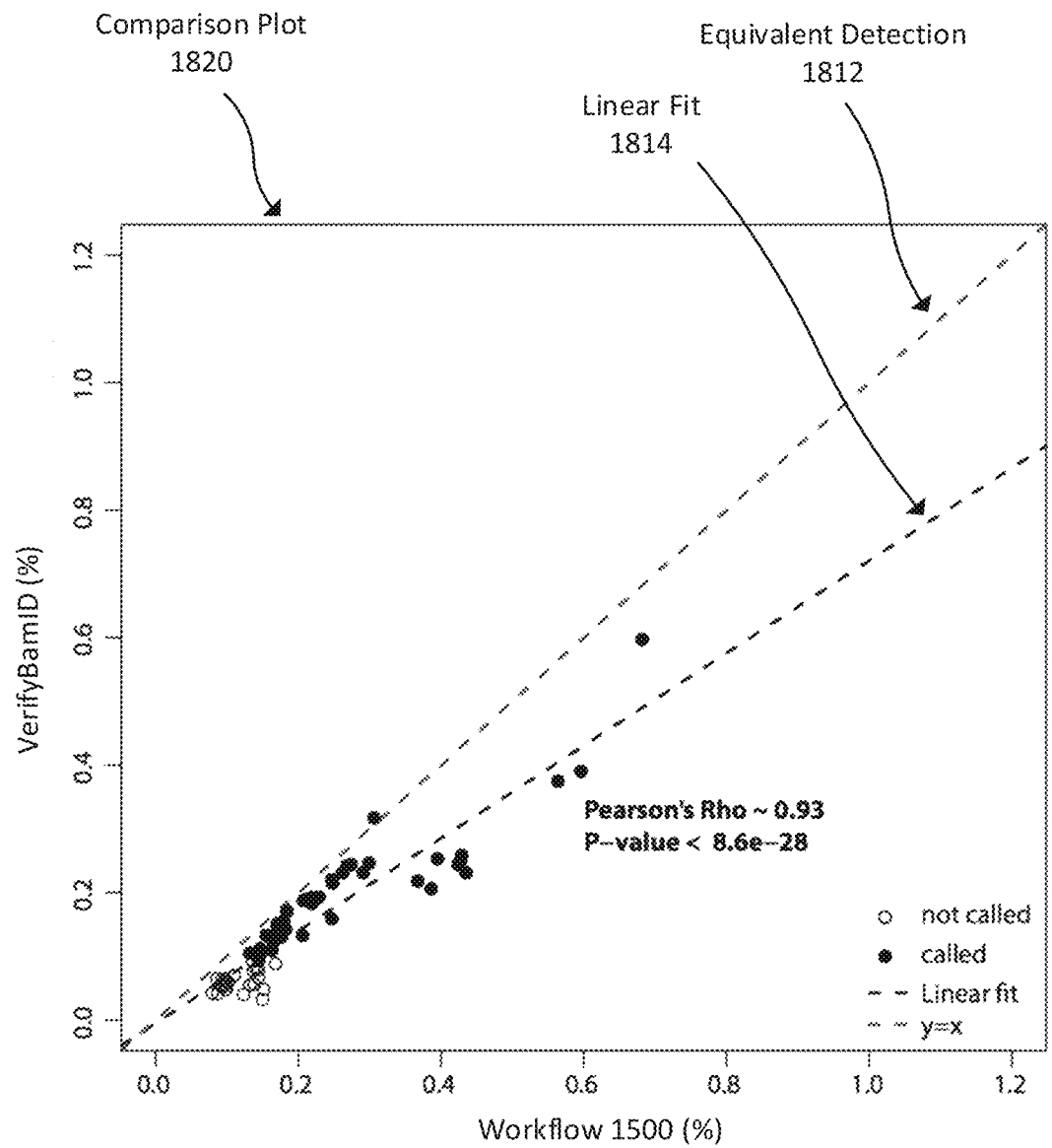

FIG. 18A-18B are comparison plots showing a comparison of contamination calls by detection workflow 1500 and alternate workflows 2 and 3. The detection workflow and alternate workflows are applied to 63 CEU samples from the 1000 genomes project to determine if the sample is contaminated and at what contamination level the sample is contaminated. Here, the samples are known to not include cancer. The closed circles are contamination events detected by both the alternate workflow and the detection workflow 1500. The open circles are contamination events detected by detection workflow 1500 and not the alternate workflow. The x-axis is the contamination level detected by contamination workflow 1500 and the y-axis is the contamination level detected by the alternate workflow. The line 1812 represents equivalent detected contamination levels and the line 1814 represents a linear fit of the determined contamination levels.

Plot 1810 compares alternate workflow 1 to the detection workflow 1500. Plot 1810 illustrates that both workflows call similar contamination events when the contamination level is above ~0.2%. Additionally, ContEst overestimates detected contamination levels when compared to workflow 1500. Plot 1820 compares alternate workflow 2 to the detection workflow 1500. Plot 1820 illustrates that both workflows call similar contamination events when the contamination level is above ~0.1%. Additionally, VeirifyBamID slightly underestimates detected contamination levels when compared to workflow 1500.

IX.C Cancer Samples from Tumors

Figure 19A:
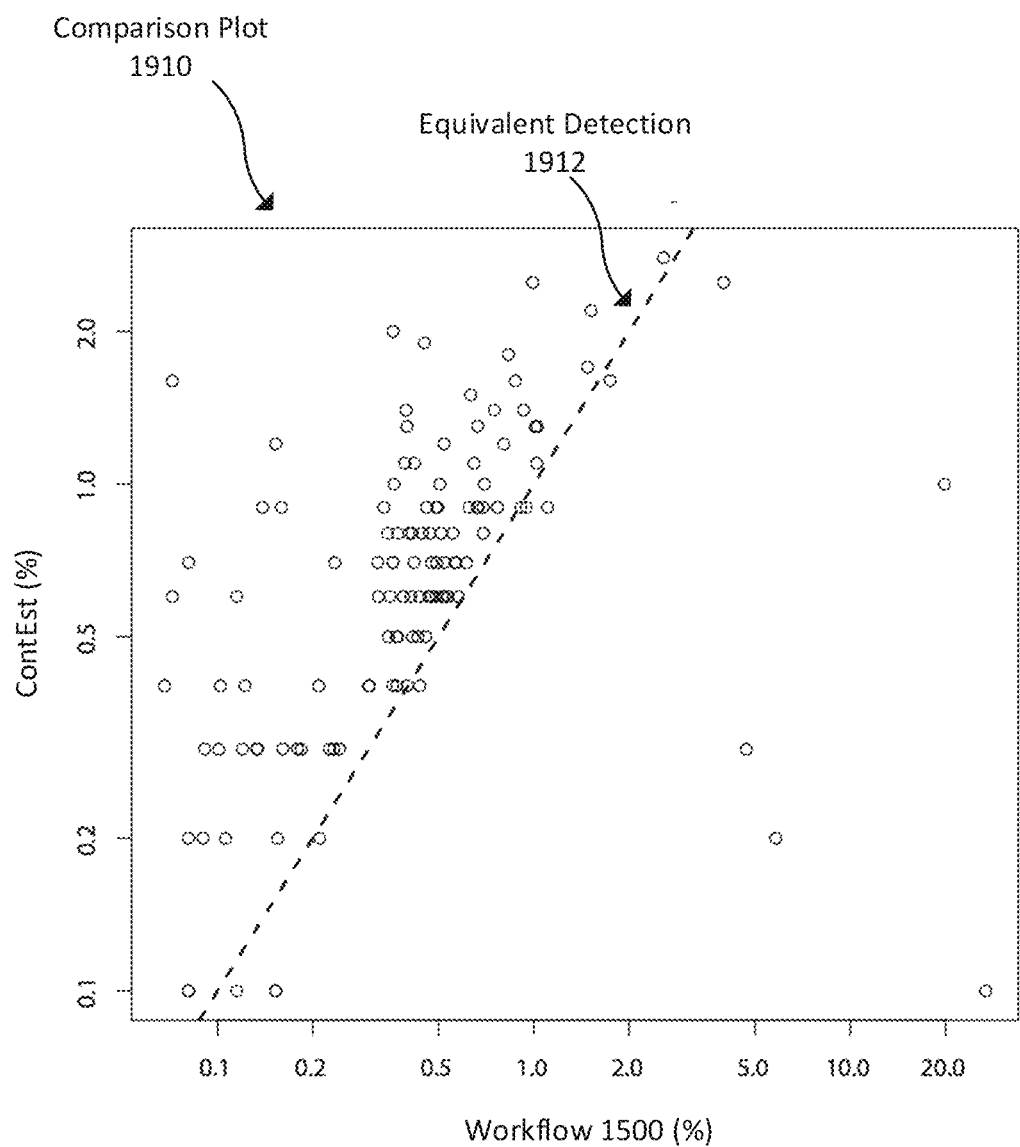
FIGS. 19A-19C are plots comparing the performance of contamination detection including loss of heterozygosity removal and alternative detection methods known in the art for detecting contamination in samples obtained from tumors, according to one example embodiment.
Figure 19B:
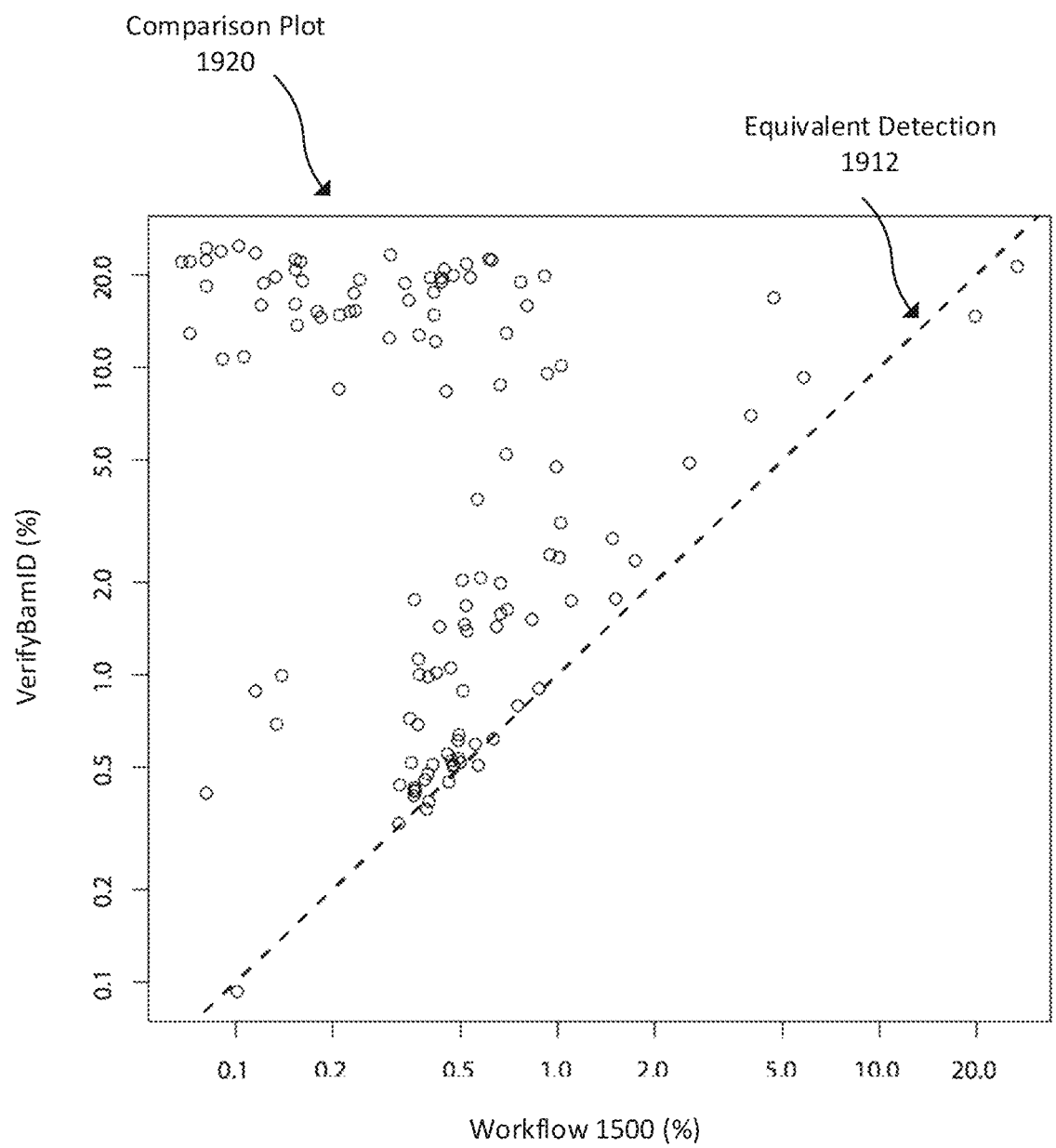
Figure 19C:
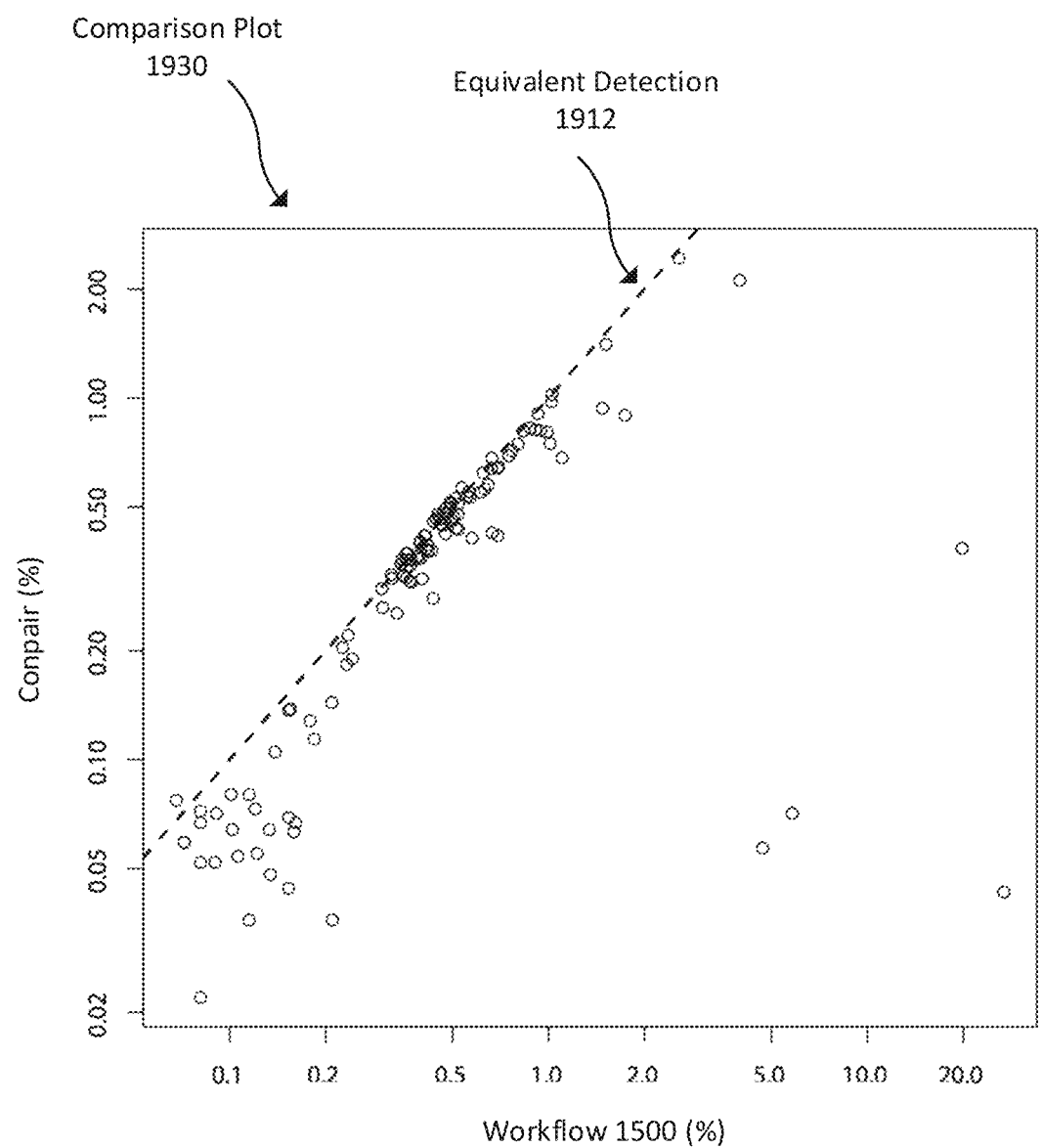

FIGS. 19A-19C are plots showing a comparison of contamination calls and detected contamination levels by detection workflow 1500 and alternate workflows 1-3. The detection workflow and alternate workflows are applied to 120 tumor samples from Exome sequence data to determine if the sample is contaminated and at what contamination level the sample is contaminated. Here, all the samples are known to include cancer. The x-axis is the contamination level detected by contamination workflow 1500 and the y-axis is the contamination level detected by the alternate workflow. The line 1912 represents equivalent detected contamination levels.

Plot 1910 compares alternate workflow 1 to the detection workflow 1500. Plot 1910 illustrates that alternate workflow 1 overestimates the contamination level compared to workflow 1500. Additionally, ContEst substantially underestimates samples contaminated at less than ~2%. Plot 1920 compares alternate workflow 2 to the detection workflow 1500. Plot 1920 illustrates that alternate workflow 2 overestimates the contamination level compared to workflow 1500. Additionally, VeirifyBamID substantially overestimates some samples with a contamination level less than ~1%. Plot 1930 illustrates that alternate workflow 3 determines similar contamination levels in samples with contamination levels between 0.2% and 2.0%. However, Conpair generally underestimates contamination levels outside that range of contamination levels.

X. Background Noise Baseline

It is important to distinguish between a contaminant signal and noise. A background noise baseline can be used to distinguish static noise that is generated during sequencing of each SNP. The background noise may be from the sequence context of a variant; some regions will have a higher noise level and some regions will have a lower noise level. In one embodiment, the noise baseline can be determined from the mean allele frequencies observed for a plurality of SNPs across healthy samples.

The background noise baseline is a noise baseline for each SNP that is based on the expected noise across a plurality of normal (uncontaminated) samples. As noted above, the background noise baseline can be captured in the background noise model of baseline batch component 420. Further, generating the contamination noise baseline can be used in any of the various contamination detection methods described herein (e.g., workflow 400 of FIG. 4, workflow 600 of FIG. 6, and workflow 1500 of FIG. 15).

In one embodiment, determining a contamination baseline can be based on the probability of observing a noise level due to errors for a homozygous sample genotype.

X.A Background Noise Workflow

Figure 20:
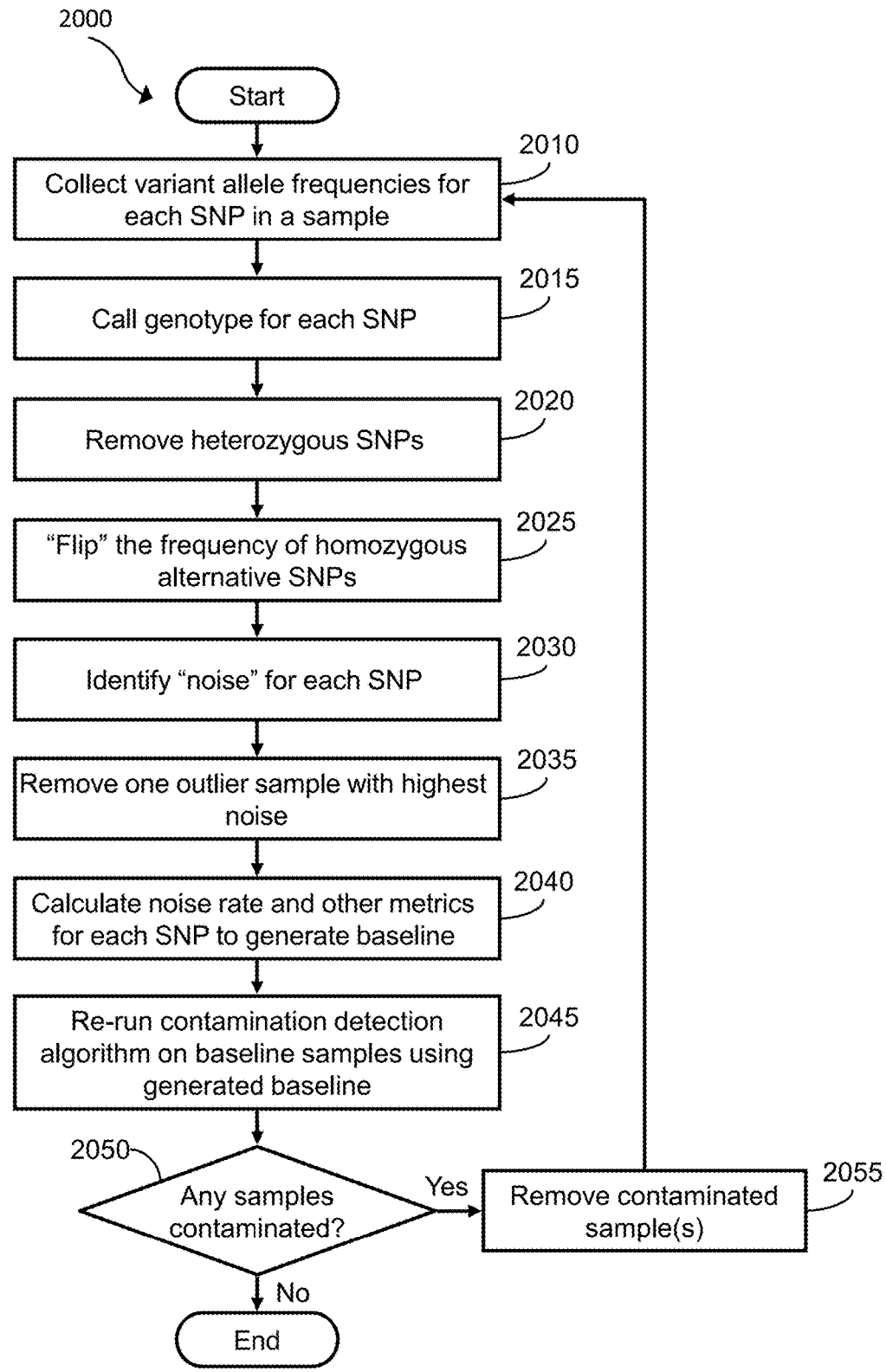
FIG. 20 illustrates a flow diagram of an example of a method for generating a contamination noise baseline, according to one example embodiment.

FIG. 20 illustrates a flow diagram of an example workflow 2000 of generating a contamination noise baseline. Workflow 2000 may include, but is not limited to, the following steps.

At a step 2010, variant allele frequencies for each SNP are collected from pileup files from a set of normal baseline samples (n=80 normal samples).

At a step 2015, the genotype for each SNP in a sample is called. For example, an allele frequency range from about 25% to about 75% is called as a heterozygous allele; an allele frequency from about less than 25% is called as a homozygous reference allele, and an allele frequency from about greater than 75% is called as a homozygous alternative allele.

At a step 2020, the heterozygous SNPs are removed.

At a step 2025, the frequency of each homozygous alternative SNP is flipped subtracting this allele frequency from 1, for example, 99.9% allele frequency becomes 0.1%. Therefore variant allele frequency from this step on corresponds to noise frequency.

At a step 2030, the deviation of the flipped frequency from 0 is determined and identified as "noise" for that SNP.

At a step 2035, for each SNP, one outlier sample with the highest noise is removed.

At a step 2040, the noise rate and other metrics for each SNP are calculated using the remaining samples to generate a baseline. Some example metrics include a heterozygous rate, homozygous rate, and compliance with Hardy-Weinberg equation and observed noise frequency.

At a step 2045, the contamination detection algorithm is run on the baseline samples using the generated baseline.

At a decision step 2050, it is determined whether any of the baseline samples are contaminated. If yes, then workflow 200 proceeds to a step 2055. If no, then the generated baseline becomes the final baseline and workflow 2000 ends.

At step 2055, the contamination noise baseline sample(s) is removed and workflow 2000 returns to step 2010.

X.B Background Noise Data

Figure 21:
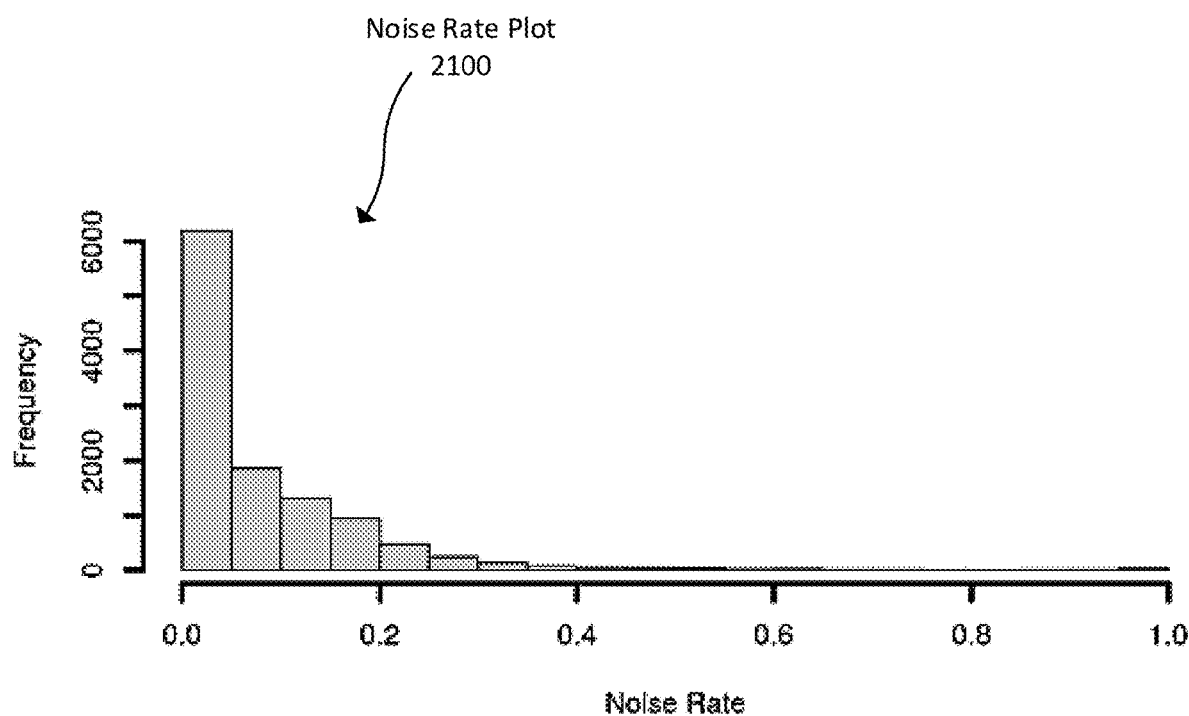
FIG. 21 is a plot showing an example of the noise rate of SNPs, according to one example embodiment.

FIG. 21 is a noise rate plot 2100 showing an example of the noise rate of SNPs. The data show that about half of the SNPs (6189 SNPs (53.71%)) had less than 5% of samples with any error. That is, for 95% of samples SNPs were called as the expected value.

Figure 22A:
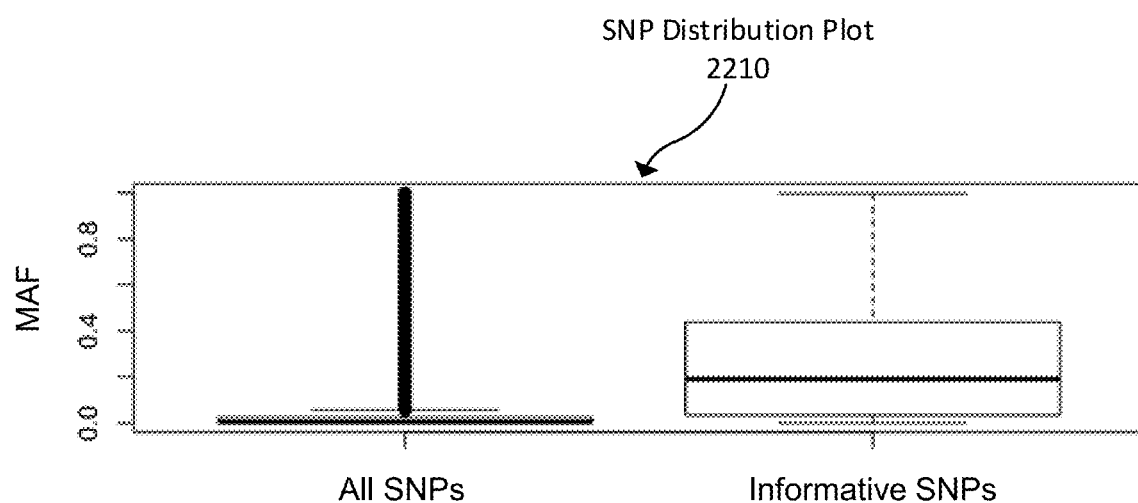
FIG. 22A is a plot showing the MAF distribution of informative SNPs compared to all SNPs, according to one example embodiment.

FIG. 22A is a SNP distribution plot 2210 showing the MAF distribution of informative SNPs compared to all SNPs. As shown, informative SNPs have higher MAFs.

Figure 22B:
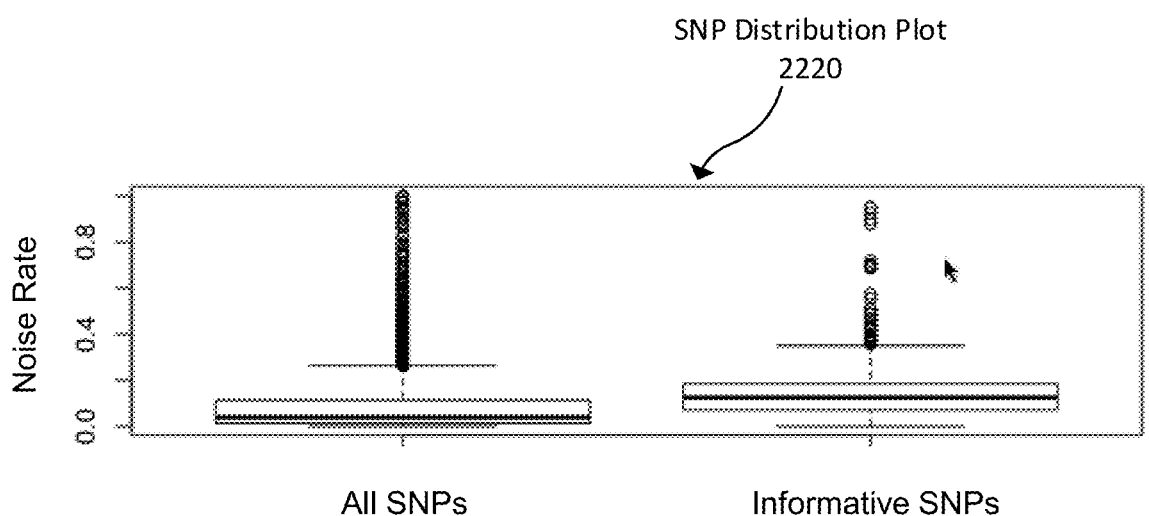
FIG. 22B is a plot showing the noise rate distribution of informative SNPs compared to all SNPs, according to one example embodiment.
Figure 23:
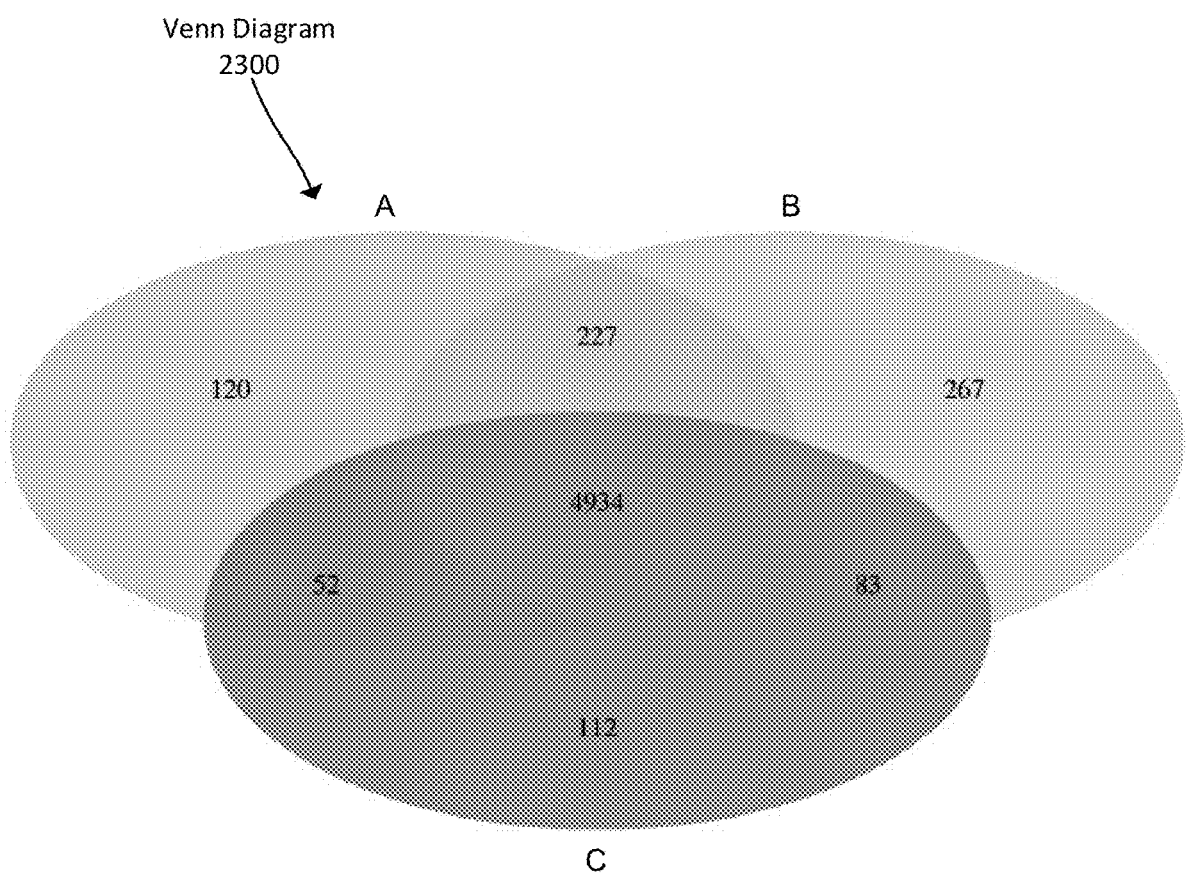
FIG. 23 is a Venn diagram showing a comparison of the contamination (noise) baselines generated for three separate studies (designated A, B, and C), according to one example embodiment.

FIG. 22B is a SNP distribution plot 2220 showing the noise rate distribution of informative SNPs compared to all SNPs. As shown, informative SNPs have a higher noise rate.

FIG. 22 is a Venn diagram 2300 showing a comparison of the contamination (noise) baselines generated for three separate studies (designated A, B, and C). The data show that the noisy SNP sites (4934) are consistent across different sample sets and are not due to some random calculation (noise rate >0.05).

Figure 24:
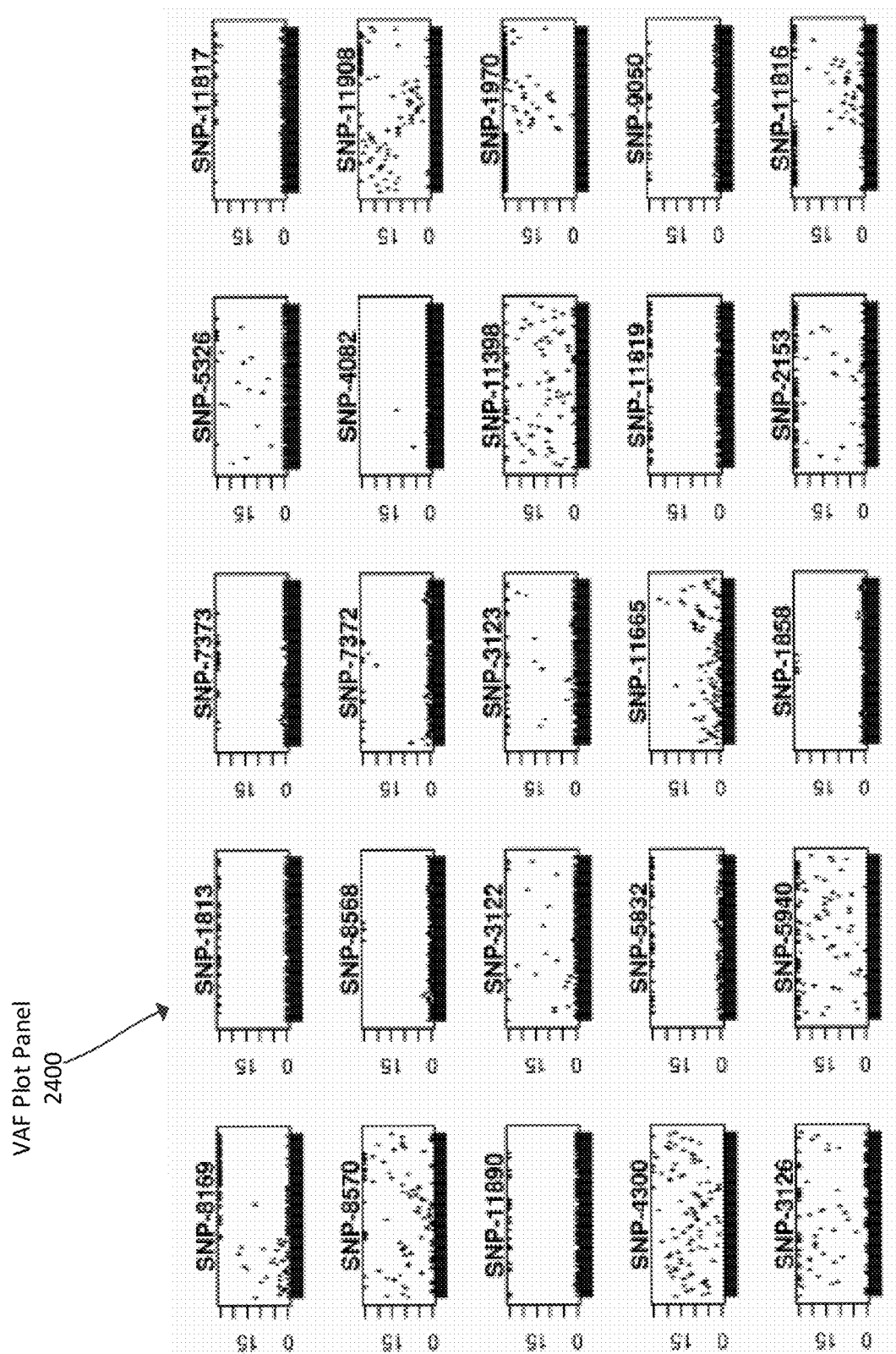
FIG. 24 is a panel of plots showing the variant allele frequencies for 25 SNPs, according to one example embodiment.

FIG. 24 is a panel 2400 of variant allele frequency (VAF) plots showing the variant allele frequencies for 25 SNPs. For each SNP, 24 samples were assessed. The divergence in the observed variant allele frequency away from zero represents noise. Some of the SNPs have very high noise across samples and may be filtered out during analysis.

Table 1 below shows an example of filtering statistics for an example starting set of 12174 SNPs. SNPs that were filtered out include 651 SNPs that had no coverage in pileup files, 57 SNPs with high error frequencies (more than 0.1% average error), 44 SNPs with high variance, 28 SNPs with low coverage, and 9 SNPs had a higher heterozygous rate (MAF) than expected.

TABLE 1

| SNP filtering statistics | |
| --- | --- |
| Total SNPs | 12174 |
| No.coverage | 651 |
| High.error | 57 |
| High.variance | 44 |
| Low.coverage | 28 |
| High.Het.Rate | 9 |
| Total.Filtered | 769* |
| Kept | 11405 |

*Some SNPs may be removed by more than one filter

X.C Background Noise in Contamination Detection

Contamination detection workflow 600 of FIG. 6 was tested using a baseline/normal sample dataset (n=84). Table 2 below shows a summary of the contaminated samples identified in the baseline/normal dataset using contamination detection method 200. Out of 84 baseline/normal samples tested, 4 samples were found to be contaminated at about 0.1% contamination level. For 2 of the samples (B2_6_CR_13 and B6_14_W044216552592), the sources of contamination were identified (B2_6_CR_13 contaminated with B2_5_W044216569928, and B6_14_W044216552592 contaminated with B6_10_W044216575078). The contaminated samples in the baseline/normal sample dataset were not detected using a robust linear regression model with a LOD of about 0.2%.

TABLE 2

| Contaminated samples in baseline/normal dataset | |
| --- | --- |
| Sample | Source |
| B2_14_CR_08 | Undetermined |
| B2_6_CR_13 | B2_5_W044216569928 |
| B6_02_W044216564538 | Undetermined |
| B6_14_W044216552592 | B6_10_W044216575078 |

XI. Output Files

Figure 25:
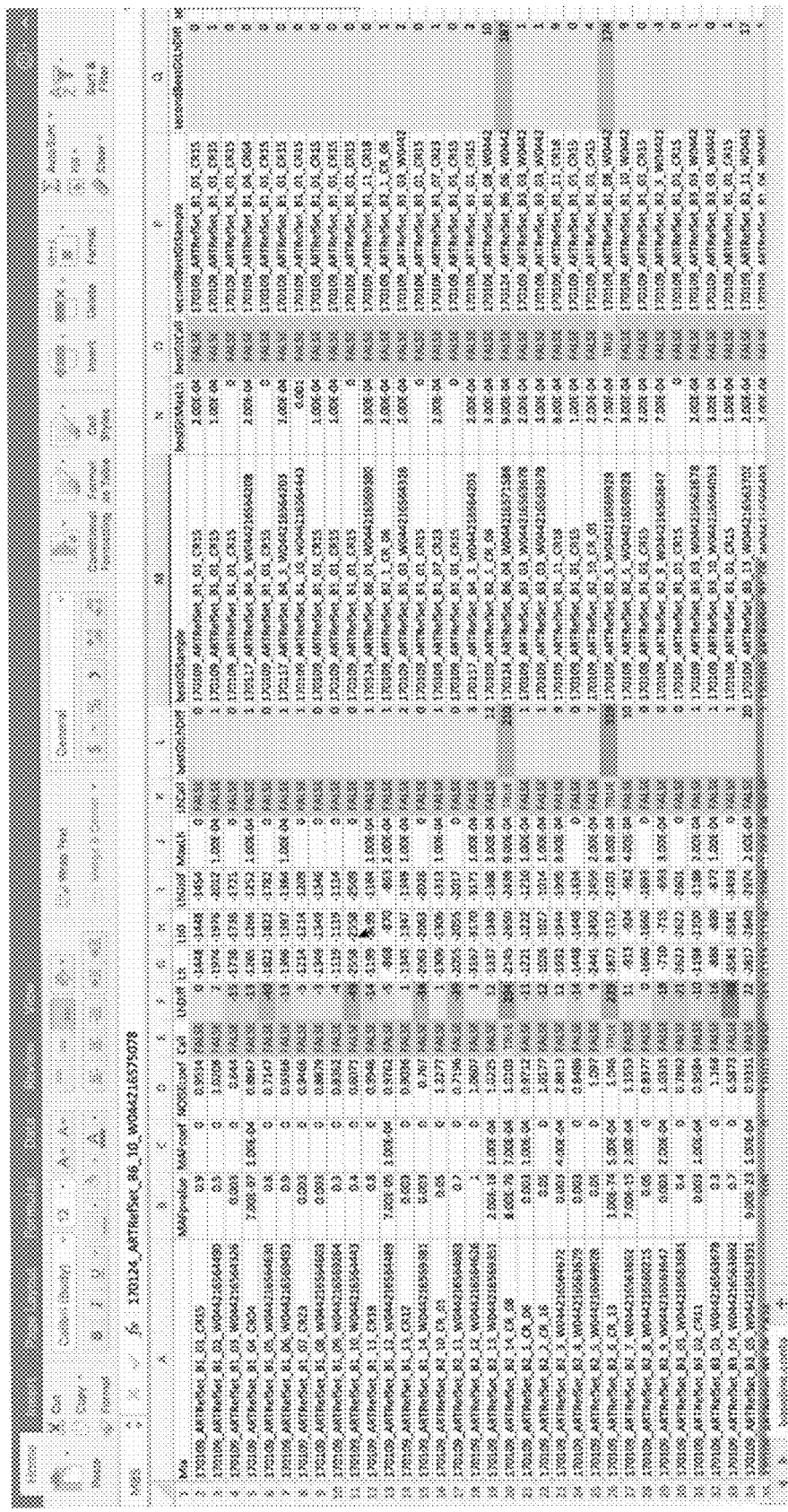
FIG. 25 is a screenshot of an example of an output file opened in MS Excel that includes information for each baseline/normal sample tested, according to one example embodiment.

FIG. 25 is a screenshot 2500 of an example of an output file 440 opened in Microsoft (MS) Excel that includes information for each baseline/normal sample tested. Each row represents a sample. In this example, both a robust linear regression model and contamination detection method 200 of FIG. 2 were used to call contamination events, and genotype probability was used as prior probability in a likelihood estimation to identify the source of contamination. Output data for the linear regression model includes, for example, MAFpvalue, MAFcoef, Noisecoef, and Call; output data for contamination detection method 200 (maximum likelihood estimation) includes LhDiff, Lh, Lh0, Lhunif, MaxLh, and LhCall; and output data for the genotype method for contaminant source identification includes bestGtSample, best GtMaxLh, and best GtCall. Samples that are called as contaminated using the linear regression model and contamination detection algorithms are indicated by "TRUE" in column E "Call" and column K "LhCall", respectively.

Figure 26:
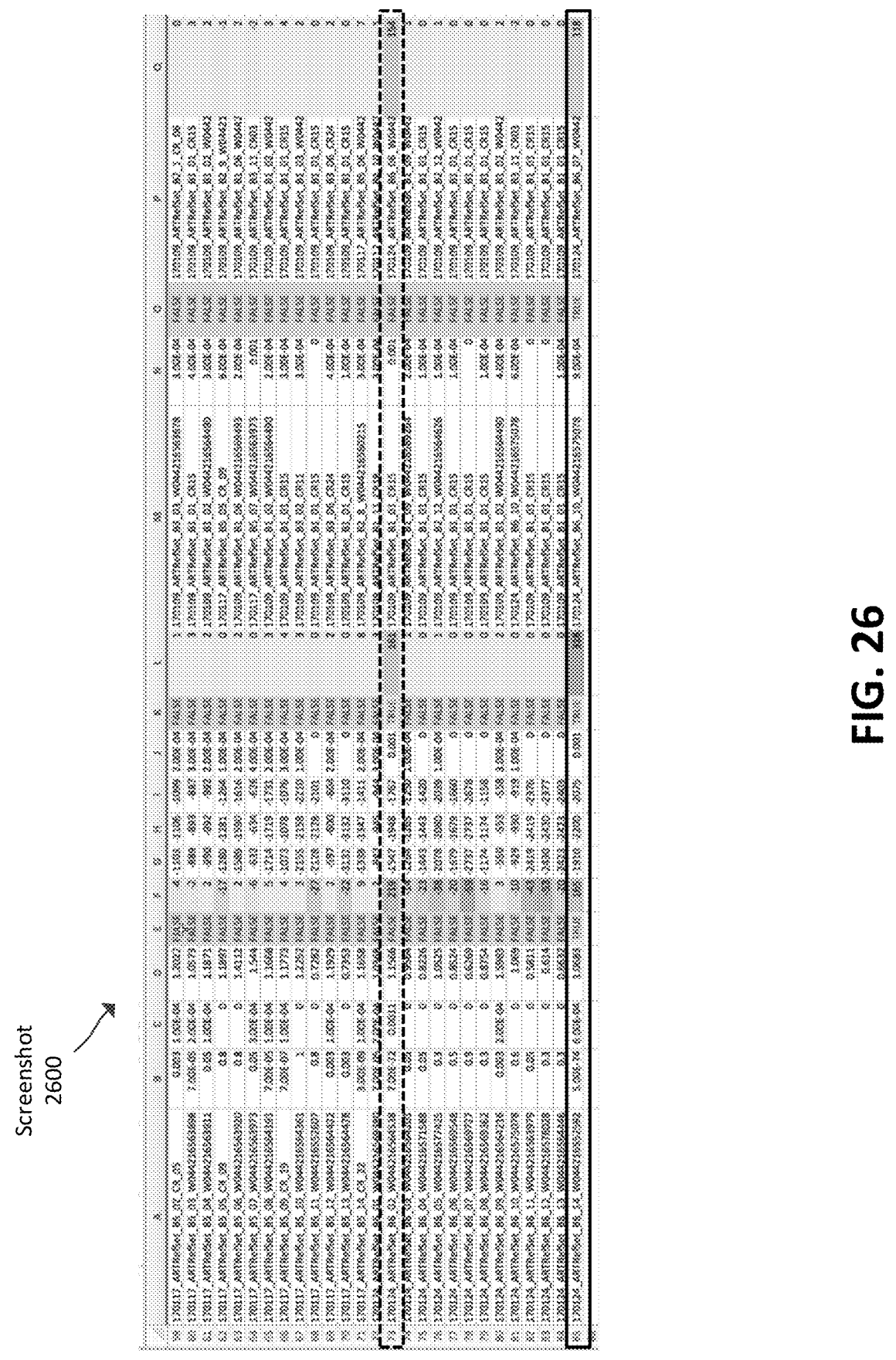

FIG. 26 is a screenshot 2600 of a portion of output file 440 of FIG. 25 that shows the analysis data for two contamination events in the baseline/normal sample dataset. Contamination of sample B6_14_WO44216552592 (row 85, indicated by boxed area) was called with the linear regression method (column E "TRUE") and detection workflow 500 (column K "TRUE"). The likelihood ratio (column F "LhDiff") was 165 compared to zero contamination hypothesis. Using genotype probabilities as prior probabilities in the likelihood estimation, one of the genotypes B6_10_WO44216575078 gave a likelihood ratio of 318 (column L "bestGtLhDiff"), which is significantly higher than the original likelihood ratio of 165. From this difference in likelihood ratios, it can be concluded that the B6_10_WO44216575078 sample is the contaminant.

Contamination of sample B6_02_WO44216564538 (row 73, indicated by dashed box area) was not called with the linear regression method (column E "FALSE"), but was called with contamination detection method 200 (column K "TRUE"). The likelihood ratio (column F "LhDiff") was 219 compared to zero contamination hypothesis. From the original likelihood ratio, it is concluded that the B6_02_WO44216564538 sample is contaminated, but the source of contamination was not identified based on genotype data for the baseline/normal dataset. That is, in this case, the genotype likelihood ratio of 161 is lower than the original likelihood ratio of 219.

Figure 27A:
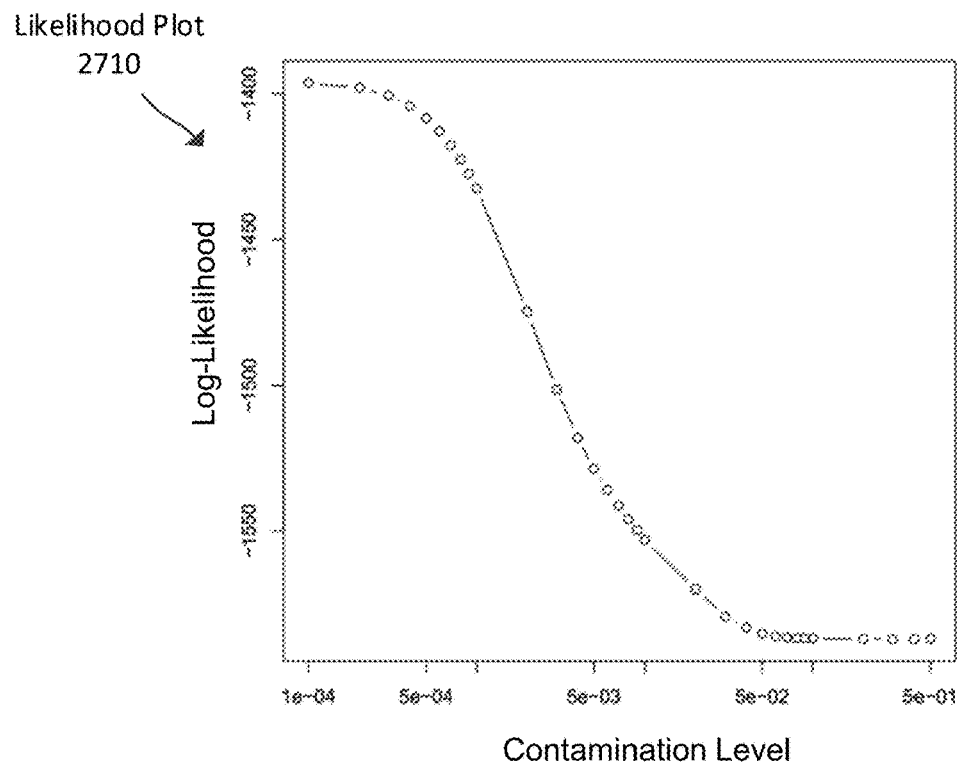
FIGS. 27A and 27B are plots showing the log-likelihood of different hypotheses of contamination levels for baseline/normal samples B1_6_WO44216569493 and B6_14_WO44216552592, according to one example embodiment.
Figure 27B:
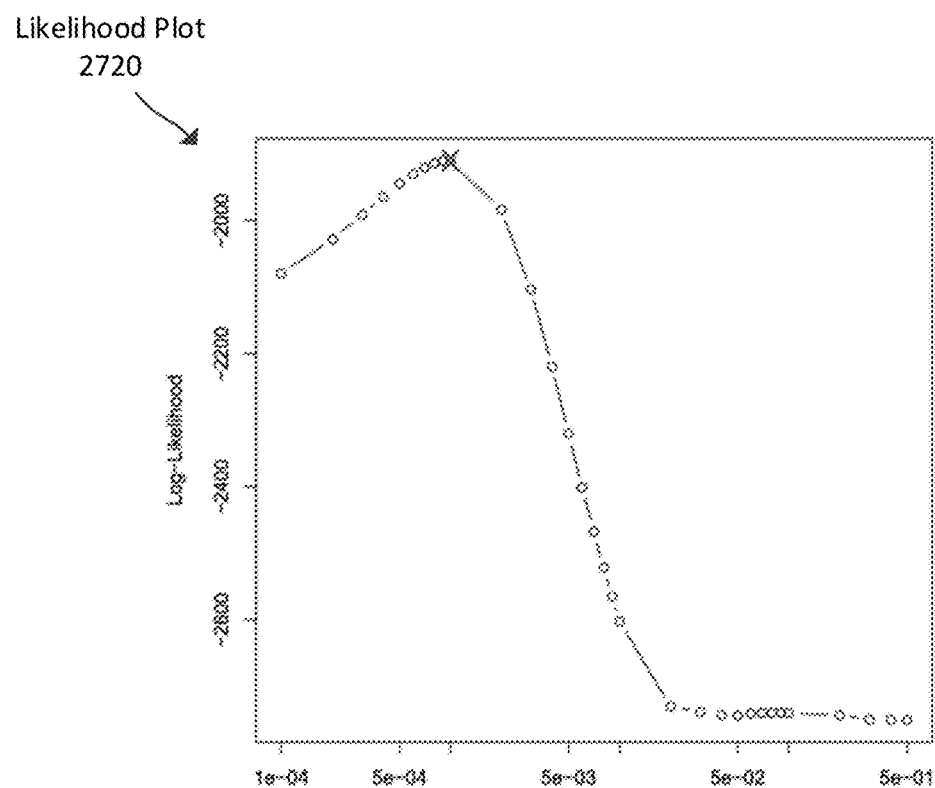

FIGS. 27A and 27B are likelihood plots 2710 and 2720, respectively, showing the log-likelihood plots 442 of different hypotheses of contamination levels for baseline/normal samples B1_6_WO44216569493 and B6_14_WO44216552592. Referring to FIG. 27A, plot 2710 shows no likelihood of contamination at different hypothesis levels of sample B1_6_WO44216569493. Referring to FIG. 27B, plot 2720 shows a peak (indicated by an "x") that indicates contamination of sample B6_14_WO44216552592.

As described above, log-likelihood plots (e.g., plot 2710 of FIG. 27A and plot 2720 of FIG. 27B) can be generated as output by the contamination detection workflow 400 of FIG. 4 and provide a ready means to visualize a contamination event.

XII. Filtering Based on Bisulfate Conversion

In some embodiments, the contamination detection workflow 400 can filter call files (such as called SNPs) to minimize the impact of bisulfite conversion. Bisulfite conversion can modify some of the nucleobases in a sequence and lead to false positive calls for contamination detection. More particularly, bisulfate conversion can cause a T to C conversion in an SNP which leads to a higher chance of detecting contamination (incorrectly). Thus, the contamination detection workflow 400 can filter the received sequences and include only SNPs with A to T and T to A SNPs. Filtering the received sequences that may have been modified by bisulfate conversion also decreases the limit of detection of the contamination detection workflow 400.

Figure 28:
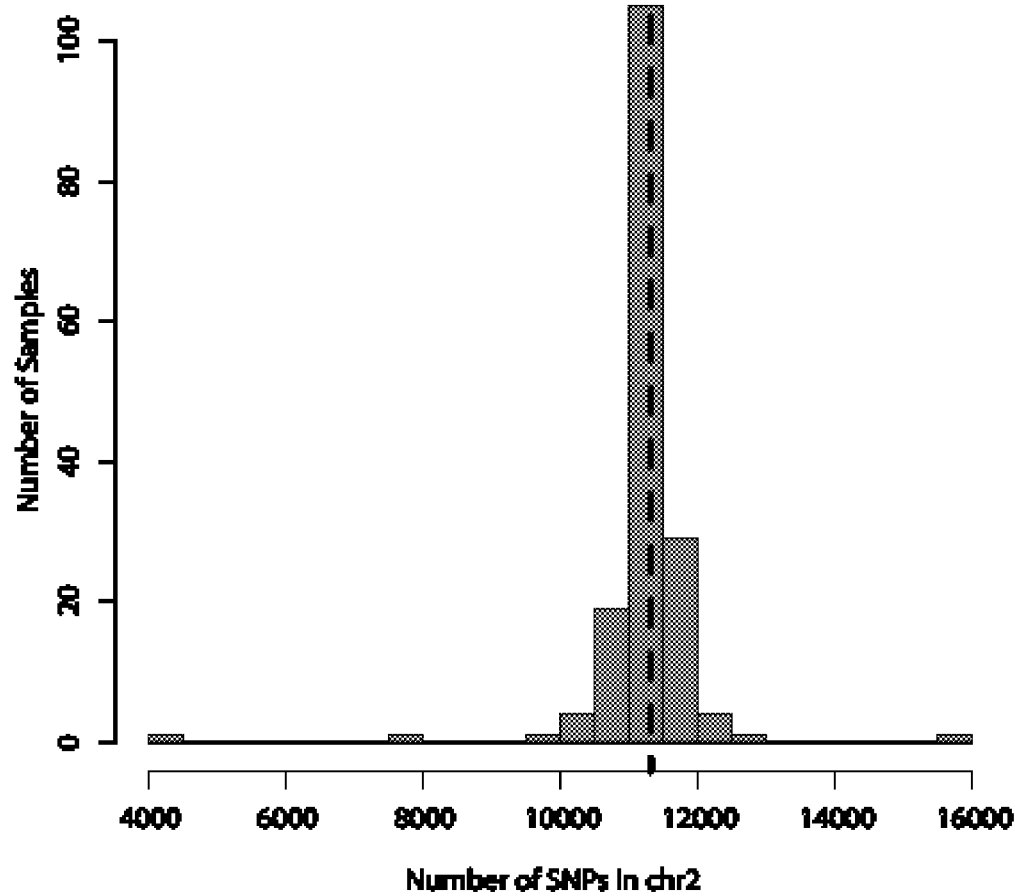
FIG. 28 is a sample distribution plot 2800 illustrating the average number of SNPs in a chromosome after the sample has been filtered based on bisulfate conversion, according to one example embodiment.

FIG. 28 is a sample distribution plot 2800 illustrating the average number of SNPs in a chromosome after the sample has been filtered based on bisulfate conversion. The x-axis is the number of SNPs in a chromosome after filtering, and the y axis is the number of samples containing that number of SNPs. Here the threshold mapQ is 60 and threshold baseQ is 36. Phred scale quality values are calculated as $-10 \log_{10} p$ where p is the probability of alignment or base being incorrect. For example, if a base has probability 0.01 of being incorrect its baseQ would be 20. MapQ considers the repeat structure of the genome, and a low value means the alignment may have multiple candidate locations. BaseQ is calculated by the instrument for a given sequencing cycle, also considering phase errors from previous cycles and represents the confidence in the base call). The only SNPs in the sample are A to T or T to A SNPs. The average number of SNPs in a sample meeting these criteria is 11,316.

Figures 29A, 29B:
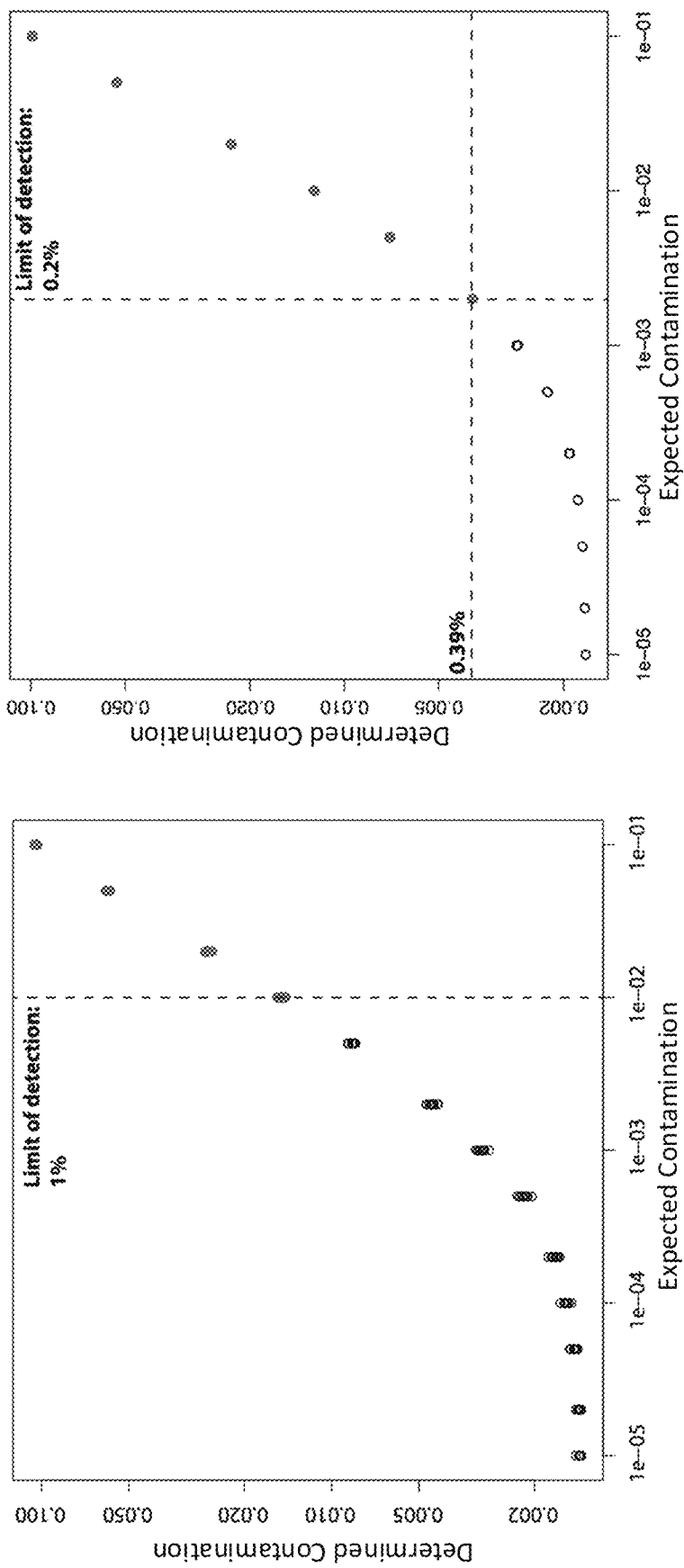
FIGS. 29A and 29B are validation plots showing the improvement in the limit of detection of contamination detection when filtering SNPs associated with bisulfate conversions, according to one example embodiment.

FIGS. 29A and 29B are validation plots showing the improvement in the limit of detection of contamination detection when filtering SNPs associated with bisulfate conversions. Each plot shows a titration experiment with a series of contamination levels between 0.001% and 0.1%. The x-axis is the expected contamination level introduced during titration and the y-axis is the measured contamination level. The limit of detection of contamination is illustrated as a horizontal dashed line in each plot. Plot 2910 shows a limit of detection of ~1% and plot 2920 shows a limit of detection ~0.2% for data using different alignment filtering paradigms.

Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer-readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

The invention claimed is:

1. A method for identifying contamination in a test sequence, the method comprising:
   receiving a plurality of test sequences including a plurality of single nucleotide polymorphisms (SNPs) that are homozygous and derived from a targeted sequencing of nucleic acid fragments from a cell-free DNA (cfDNA) sample, with each test sequence comprising one or more SNPs;
   filtering the plurality of test sequences by removing one or more test sequences wherein remaining test sequences together form a population, and wherein filtering comprises:
      generating a first distribution based on a minor allele depth of the SNPs for the cfDNA sample, a total depth of major alleles and minor alleles of the SNPs for the cfDNA sample, and a heterozygosity level,
      determining a second test sequence includes a loss of heterozygosity by applying the distribution to the one or more SNPs of the second test sequence, and
      excluding the second test sequence including the loss of heterozygosity from the population;
   determining a prior contamination probability for each SNP of the population, the prior contamination probability based on a minor allele frequency for the SNP;
   applying a contamination model including a first likelihood test to a first test sequence of the population to determine a first current contamination probability for the first test sequence using the one or more prior contamination probabilities for the one or more SNPs of the first test sequence, the first current contamination probability representing the likelihood that the first test sequence is contaminated, wherein applying the contamination model further comprises comparing a set of generated contaminated test sequences to a set of previously obtained non-contaminated test sequences as part of determining the first current contamination probability;
   detecting a contamination event by determining that the first current contamination probability of the first test sequence is above a first threshold; and
   responsive to detecting the contamination event, discarding the cfDNA sample without performing variant calling on the plurality of test sequences derived from the cfDNA sample.

2. The method of claim 1, further comprising:
   applying a second likelihood test of the contamination model to determine a second current contamination probability for the first test sequence using the one or more prior contamination probabilities for the one or more SNPs of the first test sequence; and
   determining that the first test sequence is contaminated further based on the second current contamination probability of the second likelihood test being above a threshold associated with the second likelihood test.

3. The method of claim 1, wherein the first likelihood test maximizes a likelihood function that is proportional to the probability of an event occurring in a data set given a variable.

4. The method of claim 1, wherein applying the contamination model comprises:
   generating a null hypothesis representing that the first test sequence is not contaminated;
   generating a set of contamination hypotheses representing that the first test sequence is contaminated, wherein each contamination hypothesis of the set of contamination hypotheses represents that the first test sequence is contaminated at a different contamination level; and
   applying a likelihood ratio test between the set of contamination hypotheses and the null hypothesis to obtain the first current contamination probability.

5. The method of claim 1, wherein applying the contamination model comprises:
   comparing a set of generated contaminated test sequences to an average of previously obtained test sequences to determine the first current contamination probability, the first current contamination probability associated with the likelihood that the first test sequence is contaminated at a contamination level.

6. The method of claim 1, wherein applying the contamination model comprises:
   generating a set of contamination hypotheses representing that the first test sequence is contaminated, wherein each contamination hypothesis of the set of contamination hypotheses represents that the first test sequence is contaminated at a different contamination level;
   generating a null hypothesis representing a mean minor allele frequency across one or more SNPs in a set of previously obtained test sequences at a contamination level for the set of previously obtained test sequences, wherein the contamination level of the null hypothesis is associated with the contamination hypothesis that is most likely to be contaminated; and
   applying a likelihood ratio test between the set of contamination hypotheses and the null hypothesis to obtain the current contamination probability.

7. The method of claim 1, wherein applying the contamination model further comprises:
   applying a second likelihood test to the first test sequence to determine a second contamination probability, wherein the second contamination probability represents a likelihood that observing the minor allele frequencies of the one or more SNPs of the first test sequence is due to contamination rather than due to a constant increase in background noise across all SNPs of the population.

8. The method of claim 1, wherein determining the second test sequence includes the loss of heterozygosity further comprises:
   generating a null hypothesis that the test sequences are heterozygous based on the first distribution;
   generating a first hypothesis that the test sequences include at least the second test sequence including the loss of heterozygosity based on a loss of heterozygosity level; and
   applying a heterozygosity contamination model including a heterozygosity likelihood test using at least the null hypothesis and the first hypothesis to obtain a heterozygosity probability representing the likelihood that the second test sequence includes the loss of heterozygosity.

9. The method of claim 8, wherein the first hypothesis is represented by a second distribution based on the minor allele depth of the SNPs for the cfDNA sample, the total depth of major alleles and minor alleles of the SNPs for the cfDNA sample, and a loss of heterozygosity level.

10. The method of claim 8, wherein determining the second test sequence includes the loss of heterozygosity is based on the heterozygosity probability representing the likelihood the second test sequence includes the loss of heterozygosity.

11. The method of claim 8, wherein determining the second test sequence includes the loss of heterozygosity further comprises:
applying the contamination model including the first likelihood test to the second test sequence to obtain a likelihood that the second test sequence is contaminated; and
determining the second test sequence includes the loss of heterozygosity based on a differential probability representing a difference in the likelihood that the second test sequence includes the loss of heterozygosity and the likelihood that the second test sequence is contaminated.

12. The method of claim 11, wherein determining the second test sequence includes the loss of heterozygosity is based on the differential probability being above a third threshold.

13. The method of claim 11, wherein the second test sequence is excluded if the likelihood that the second test sequence includes a loss of heterozygosity is larger than the likelihood that the second test sequence is contaminated.

14. The method of claim 1, wherein each test sequence of the plurality of test sequences is associated with at least one sequence batch of a plurality of sequence batches, and further comprising:
determining a contamination source for a sequence batch of the plurality of sequence batches by:
identifying a contaminated SNP from the sequence batch using the contamination model, the contaminated SNP associated with a candidate test sequence of the sequence batch, and
applying a contamination source model to one or more SNPs of the sequence batch based on the contaminated SNP and the prior contamination probabilities of the test sequences associated with the sequence batch to determine a confidence score reflecting the likelihood that the candidate test sequence is the contamination source.

15. The method of claim 14, wherein the contamination source model is further based on a genotype of the sequence batch.

16. The method of claim 1, wherein filtering the plurality of test sequences comprises:
identifying a conversion type for each SNP of the plurality of test sequences;
removing at least one SNP from the plurality of test sequences based on the conversion type.

17. The method of claim 16, wherein the remaining SNPs of the plurality of test sequences include either adenine to thymine conversions or thymine to adenine conversions.

18. The method of claim 16, wherein the conversion type of the at least one removed SNP is a result of a bisulfite conversion.

19. The method of claim 1, further comprising:
performing targeted sequencing of the cell-free DNA (cfDNA) sample to generate the plurality of test sequences.

* * * * *